United States Patent [19]
Pamukcu et al.

[11] Patent Number: 5,942,520
[45] Date of Patent: Aug. 24, 1999

[54] METHOD FOR INHIBITING NEOPLASTIC CELLS BY EXPOSURE TO SUBSTITUTED N-CYCLOALKYLMETHYL-1-H-PYRAZOLO (3, 4-B) QUINOLONE-4 AMINES

[75] Inventors: Rifat Pamukcu, Spring House; Gary A. Piazza, Doylestown, both of Pa.

[73] Assignee: Cell Pathways, Inc., Horsham, Pa.

[21] Appl. No.: 09/014,409

[22] Filed: Jan. 27, 1998

[51] Int. Cl.$^6$ .......................... A61K 31/44; A61K 31/232
[52] U.S. Cl. .......................... 514/293; 514/293; 514/232.8
[58] Field of Search ................................... 514/293, 232.8

[56] References Cited

U.S. PATENT DOCUMENTS

| | | | |
|---|---|---|---|
| 3,031,450 | 4/1962 | Fischer et al. | 260/247.5 |
| 3,161,654 | 12/1964 | Shen | 260/319 |
| 3,322,755 | 5/1967 | Roch et al. | 260/246 |
| 3,517,005 | 6/1970 | Cronin et al. | 260/256.4 |
| 3,594,480 | 7/1971 | Cronin et al. | 424/250 |
| 3,647,858 | 3/1972 | Hinkley et al. | 260/470 |
| 3,654,349 | 4/1972 | Shen et al. | 260/515 |
| 3,780,040 | 12/1973 | Schnettler et al. | 260/256.5 |
| 3,812,127 | 5/1974 | Cronin et al. | 260/268 |
| 3,819,631 | 6/1974 | Broughton et al. | 260/256.4 |
| 3,920,636 | 11/1975 | Takahasi et al. | 260/240 |
| 4,001,237 | 1/1977 | Partyka et al. | 260/256.4 |
| 4,001,238 | 1/1977 | Partyka et al. | 260/256.4 |
| 4,039,544 | 8/1977 | Broughton et al. | 260/256.4 |
| 4,060,615 | 11/1977 | Matier et al. | 424/251 |
| 4,079,057 | 3/1978 | Juby et al. | 260/256.5 |
| 4,098,788 | 7/1978 | Crenshaw et al. | 544/293 |
| 4,101,548 | 7/1978 | Crenshaw et al. | 544/284 |
| 4,102,885 | 7/1978 | Crenshaw et al. | 544/283 |
| 4,138,561 | 2/1979 | Crenshaw et al. | 544/284 |
| 4,146,718 | 3/1979 | Jenks et al. | 544/292 |
| 4,161,595 | 7/1979 | Kaplan et al. | 544/284 |
| 4,171,363 | 10/1979 | Crenshaw et al. | 424/251 |
| 4,208,521 | 6/1980 | Crenshaw et al. | 544/250 |
| 4,209,623 | 6/1980 | Juby | 544/319 |
| 4,423,075 | 12/1983 | Dvornik et al. | 424/317 |
| 4,460,590 | 7/1984 | Möller | 424/251 |
| 4,460,591 | 7/1984 | DeGraw et al. | 424/251 |
| 4,880,810 | 11/1989 | Lowe, III et al. | 514/258 |
| 4,885,301 | 12/1989 | Coates | 514/263 |
| 4,923,874 | 5/1990 | McMahon et al. | 514/258 |
| 5,073,559 | 12/1991 | Coates | 514/262 |
| 5,147,875 | 9/1992 | Coates et al. | 514/259 |
| 5,223,501 | 6/1993 | Charkravarty et al. | 514/258 |
| 5,250,535 | 10/1993 | Verheyden et al. | 514/262 |
| 5,254,571 | 10/1993 | Coates et al. | 514/344 |
| 5,358,952 | 10/1994 | Moschel et al. | 514/262 |
| 5,401,774 | 3/1995 | Pamukcu et al. | 514/569 |
| 5,439,895 | 8/1995 | Lee et al. | 514/63 |
| 5,488,055 | 1/1996 | Kumar et al. | 514/293 |
| 5,614,530 | 3/1997 | Kumar et al. | 514/293 |
| 5,614,627 | 3/1997 | Takase et al. | 544/293 |
| 5,852,035 | 12/1998 | Pamukcu et al. | 514/293 |

FOREIGN PATENT DOCUMENTS

| | | |
|---|---|---|
| 0 347146 A2 | 12/1989 | European Pat. Off. |
| 0 349239 A2 | 1/1990 | European Pat. Off. |
| 0 351058 | 1/1990 | European Pat. Off. |
| 0 352960 A2 | 1/1990 | European Pat. Off. |
| 0 395 328 A2 | 10/1990 | European Pat. Off. |
| 0 428268 A2 | 5/1991 | European Pat. Off. |
| 0 463756 A1 | 1/1992 | European Pat. Off. |
| 0 485157 A2 | 5/1992 | European Pat. Off. |
| 0 485158 A2 | 5/1992 | European Pat. Off. |
| 0 485171 A2 | 5/1992 | European Pat. Off. |
| 0 485172 A2 | 5/1992 | European Pat. Off. |
| 0 485173 A2 | 5/1992 | European Pat. Off. |
| 0 508586 A1 | 10/1992 | European Pat. Off. |
| 0 526004 A1 | 2/1993 | European Pat. Off. |
| 0 607439 A1 | 7/1994 | European Pat. Off. |
| 3038166 | 5/1981 | Germany. |
| 274218 | 12/1989 | Germany. |
| 56-53659 | 5/1981 | Japan. |
| 57-167974 | 10/1982 | Japan. |
| 807826 | 1/1959 | United Kingdom. |
| 2063249 | 6/1981 | United Kingdom. |
| WO 92/03419 | 3/1992 | WIPO. |
| WO 93/07149 | 4/1993 | WIPO. |
| WO 93/12095 | 6/1993 | WIPO. |
| WO 94/05661 | 3/1994 | WIPO. |
| WO 97/03985 | 2/1997 | WIPO. |

OTHER PUBLICATIONS

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

Gilman, S.C. et al., Nonsteroidal Anti–inflammatory Drugs in Cancer Therapy, (1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

(List continued on next page.)

*Primary Examiner*—Phyllis G. Spivack
*Attorney, Agent, or Firm*—Robert W. Stevenson

[57] ABSTRACT

A method for inhibiting neoplastic cells and related conditions by exposing them to substituted N-cycloalkylmethyl-1H-pyrazolo[3,4-b]quinolin-4-amines.

15 Claims, No Drawings

OTHER PUBLICATIONS

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225, Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibitioin of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheralmorphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichter, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan, et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter et al., Chemotherapy of Cancer, $2^{nd}$ Ed., John Wiley & Sons, NY, NY, 1981, pp. 362–365.

Biddle, William et al., Antineoplastic Effect of the Pyrimido–Pyrimidine Derivative: RA 233, Pathologie Biologie, Jan., 1984, pp. 9–13.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

METHOD FOR INHIBITING NEOPLASTIC CELLS BY EXPOSURE TO SUBSTITUTED N-CYCLOALKYLMETHYL-1-H-PYRAZOLO (3, 4-B) QUINOLONE-4 AMINES

TECHNICAL FIELD

This invention relates to a method for the selective inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation which can be fatal. Overall, about $2.5 billion is spent annually in the United States in colon cancer treatment and prevention.

In the breast, breast cancer is often treated surgically, often by radical mastectomy with its painful and emotional aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, or as sometimes referred to as "programmed cell death." Apoptosis naturally occurs in virtually all tissues of the body, and especially in self-renewing tissues such as bone marrow, immune cells, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of nonspecific cytotoxicity of the drugs, include hair loss, weight loss, vomiting, immune suppression and other toxicities. For this reason, there is a need to identify new drug candidates for therapy of patients with precancerous lesions that do not have such serious side effects in humans.

In recent years, several nonsteroidal anti-inflammatory drugs ("NSAIDs"), originally developed to treat arthritis, have shown effectiveness in inhibiting and eliminating colonic polyps. Polyps virtually disappear when the patients take such drugs, particularly when the NSAID sulindac is administered. However, the prophylactic use of currently available NSAIDs, even in polyposis syndrome patients, is marked by severe side reactions that include gastrointestinal irritations, perforations, ulcerations and kidney toxicity. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an antiarthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions.

The compounds of that are useful in the methods of this invention include those of Formula I:

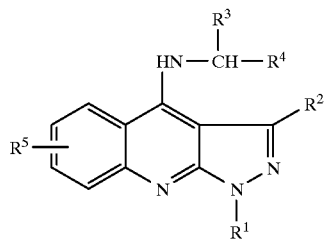

wherein $R_1$ is lower-alkyl, phenyl-lower-alkyl, or cycloalkyl; $R_2$ is hydrogen, or lower-alkyl; $R_3$ is hydrogen, lower-alkyl, or hydroxylower-alkyl;

$R_4$ is cycloalkyl or cylcoalkyl substituted by from one to two, the same or different, substituents selected from the group consisting of lower-alkoxycarbonyl, carboxy, lower-alkylthio-lower-alkoxycarbonyl, hydroxylower-alkyl, hydroxy, oxo, lower-alkoxy, lower-alkyl, and halogen; and $R_5$ is from one to three, the same or different, substituents selected from the group consisting of hydrogen, lower-alkoxy, hydroxy, dilower-alkylamino-lower-alkoxy, carboxylower-alkoxy, lower-alkoxycarbonyl-lower-alkoxy, nitro, polyhydroxylower-alkoxy, amino, epoxylower-alkoxy, carboxy, lower-alkanoylamino, lower-alkoxycarbonyl, pyridinyl, 4-morpholinyl-lower-alkoxy, lower-alkylsulfonyl, cyano, 1-imidazolyl, halogen, dilower-alkylaminosulfonyl, oxadiazolyl (or oxadiazolyl substituted on any available carbon atom thereof by lower-alkyl), lower-alkylsulfinyl, 1-pyrazolyl (or 1-pyrazolyl substituted on any available carbon atom thereof by lower-alkyl), trifluoromethylsulfonyl, lower-alkenyl, lower-alkyl, and lower-alkynyl; or a pharmaceutically acceptable acid-addition salt and/or hydrate and/or solvate thereof, or, where applicable, a stereoisomer or a racemic mixture thereof.

DETAILED DESCRIPTION OF THE INVENTION

As discussed above, this invention involves the use of compounds of Formula I for treating a patient with neoplasia, for example cancerous or precancerous lesions. Preferred compounds of Formula I above useful in the practice of the methods of this invention are those where $R_1$, $R_2$ and $R_3$ are as defined above;

$R_4$ is cycloalkyl or cylcoalkyl substituted by one substituent selected from the group consisting of lower-alkoxycarbonyl, lower-alkylthio-lower-alkoxycarbonyl, hydroxylower-alkyl, hydroxy, and oxo; and $R_5$ is from one to two, the same or different, substituents selected from the group consisting of hydrogen, lower-alkoxy, hydroxy, dilower-alkylamino-lower-alkoxy, carboxylower-alkoxy, nitro, polyhydroxylower-alkoxy, amino, epoxylower-alkoxy, carboxy, lower-alkanoylamino, lower-alkoxycarbonyl, pyridinyl, 4-morpholinyl-lower-alkoxy, lower-alkylsulfonyl, cyano, 1-imidazolyl, halogen, dilower-alkylaminosulfonyl, oxadiazolyl substituted on any available carbon atom thereof by lower-alkyl, lower-alkylsulfinyl, 1-pyrazolyl (or 1-pyrazolyl substituted on any available carbon atom thereof by lower-alkyl), trifluoromethylsulfonyl, and lower-alkenyl.

Particularly preferred compounds of Formula I above useful in the practice of the methods of this invention are those wherein $R_1$ is ethyl, isopropyl, benzyl, or cyclopentyl; $R_2$ is hydrogen, or methyl; $R_3$ is hydrogen, methyl, ethyl, or hydroxymethyl; and $R_4$ and $R_5$ are as defined directly above.

The most preferred compounds of the Formula I above useful in the practice of the methods of this invention are those wherein $R_1$ is ethyl, isopropyl, benzyl, or cyclopentyl; $R_2$ is hydrogen, or methyl; $R_3$ is hydrogen, methyl, ethyl, or hydroxymethyl; $R_4$ is cycloalkyl selected from the group consisting of cyclohexyl, cyclopropyl, and adamantyl or said cycloalkyl group substituted by one substituent selected from the group consisting of methoxycarbonyl, methylthiomethoxycarbonyl, hydroxymethyl, hydroxy, and oxo; and $R_5$ is from one to two, the same or different, substituents selected from the group consisting of hydrogen, methoxy, hydroxy, 2-(dimethylamino) ethoxy, carboxymethoxy, nitro, 2,3-dihydroxypropoxy, amino, 2,3-epoxypropoxy, 1-carboxyethoxy, carboxy, acetylamino, methoxycarbonyl, pyridinyl, 2-(4-morpholinyl) ethoxy, methylsulfonyl, cyano, 1-imidazolyl, bromo, diethylaminosulfonyl, 5-methyl-3-(1,2,4-oxadiazolyl), methylsulfinyl, 4-methyl-1-pyrazolyl, 1-pyrazolyl, trifluoromethylsulfonyl, and ethenyl. An example of a most preferred compound for practicing this invention is 1-ethyl-6-nitro-N-[S(+)-1-(cyclohexyl)ethyl]-1H-pyrazolo[3,4-b]quinolin-4-amine.

The term "lower-alkyl" as used herein means linear or branched hydrocarbon chains having from one to about four carbon atoms and thus includes methyl, ethyl, propyl, isopropyl, n-butyl, sec-butyl, and the like.

The term "lower-alkoxy" means linear or branched alkyloxy substituents having from one to about four carbon atoms and thus includes methoxy, ethoxy, propoxy, isopropoxy, butoxy, sec-butoxy, and the like.

The terms halogen, halide, or halo as used herein mean bromine, chlorine, iodine or fluorine.

The term "lower-alkenyl" means branched or unbranched unsaturated hydrocarbon radicals of from two to about four carbon atoms and thus includes 1-ethenyl, 1-propenyl, 2-propenyl, 1-methyl-2-propenyl, isopropenyl, 2-butenyl, isobutenyl, and the like.

The term "cycloalkyl" means bridged or unbridged hydrocarbon ring systems having from three to about 10 carbon atoms and thus includes cyclopropyl, cyclobutyl, cyclopentyl, cyclohexyl, cycloheptyl, cyclooctyl, cyclodecyl, norbornyl, adamantyl, and the like.

The term "polyhydroxylower-alkoxy" as used herein means lower-alkoxy as defined above which is substituted by from two to about four hydroxy groups none of which are attached to the C1 carbon atom and thus includes 2,3-dihydroxypropoxy, 3,4-dihydroxybutoxy, and the like.

The term "epoxylower-alkoxy" as used herein means lower-alkoxy as defined above in which the lower-alkoxy group also contains an epoxy group which is bonded to other than the C1 carbon atom and thus includes 2,3-epoxypropoxy, 3,4-epoxybutoxy, and the like.

The term "lower-alkanoyl" as used herein means linear or branched hydrocarbon chains having two to about four carbon atoms and thus includes acetyl, propionyl, butyryl, isobutyryl, and the like.

The term "lower-alkynyl" as used herein means branched or unbranched unsaturated hydrocarbon radicals of from two to about four carbon atoms and thus includes 1-ethynyl, 1-propynyl, 2-propynyl, 2-butynyl, 1-methyl-2-propynyl, and the like.

Preferably, such compounds are administered without therapeutic amounts of an NSAID.

The present invention is also a method of treating mammals with precancerous lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of formula I, wherein $R_1$ through $R_6$ are defined as above.

In still another form, the invention is a method of inducing apoptosis in human cells by exposing those cells to an effective amount of compounds of Formula I to those cells sensitive to such a compound.

As used herein, the term "precancerous lesion" includes syndromes represented by abnormal neoplastic, including dysplastic, changes of tissue. Examples include precancerous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, and colon cancer.

As used herein, the term "neoplasm" refers to both precancerous and cancerous lesions.

Compounds useful in the methods of this invention may be formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories that may contain, in addition to the compounds of Formula I, excipients such as cocoa butter or a suppository wax.

The pharmaceutically acceptable carrier and compounds of this invention are formulated into unit dosage forms for administration to a patient. The dosage levels of active ingredient (i.e. compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g. a box or bottle, or both) with suitable printed material (e.g. a package insert) containing indications, directions for use, etc.

The synthesis of compounds useful in practicing this invention is described in U.S. Pat. No. 5,488,055 as shown in the following Schemes:

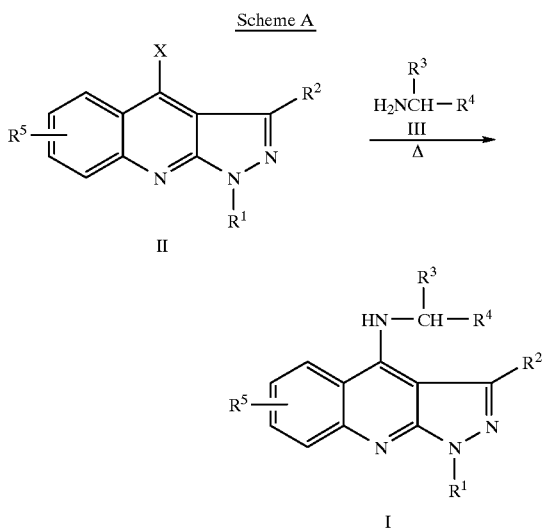

Scheme A

In Scheme A, a suitably substituted 4-halo-1H-pyrazolo[3,4-b]quinoline of the formula II, wherein X is a halogen, preferably chlorine, in a suitable organic solvent, such as dimethylsulfoxide, is treated with at least one mole of a suitably substituted amine of the formula III, optionally in the presence of at least one mole of a suitable base, such as triethylamine, at a temperature in the range of about room temperature up to the boiling point of the solvent used, preferably at a temperature in the range of about 80° C. up to the boiling point of the solvent used, to afford the substituted 1H-pyrazolo[3,4-b]quinolin-4-amines of Formula I.

Simple chemical transformations which are conventional and well known to those skilled in the art of chemistry can be used for effecting changes in the functional groups of the compounds of Formula I. For example, treatment of acids with reducing agents, e.g. LAH, to afford the corresponding alcohols, the dealkylation of aryl ethers to afford the corresponding phenol derivatives, treatment of phenol derivatives with alkylating agents to afford the corresponding ether derivatives, the acid catalyzed ring opening of epoxides to afford the corresponding diols, the catalytic reduction of nitro derivatives to afford the corresponding amines, oxidation of alcohols to afford the corresponding oxo derivatives, the treatment of aryl halides with carbon monoxide in the presence of a suitable lower-alkanol and a suitable catalyst, e.g. $Pd(Ph_3)_2Cl_2$, to afford the corresponding lower-alkoxycarbonyl substituted aryl derivatives, the hydrolysis of esters to afford the corresponding acid derivatives, the treatment of aryl halides with CuCN or a mixture of CuCN/NaCN to afford the corresponding nitrile derivatives, the treatment of nitriles with hydroxylamine hydrochloride to afford the corresponding oxime derivatives, the treatment of aryl halides with nucleophilic aromatic heterocycles, such as pyrazole and imidazole derivatives, to afford the corresponding aromatic heterocycle substituted aryl derivatives, and the treatment of aryl halides with (lower-alkenyl)Sn(lower-alkyl)3 derivatives in the presence of a suitable catalyst, e.g. $Pd(Ph_3)_2Cl_2$, to afford the corresponding lower-alkenyl substituted aryl derivatives.

It will be appreciated that the compounds of the Formula I can possess one or more asymmetric carbon atoms and are thus capable of existing in a number of stereoisomeric forms, i.e. enantiomers and diastereomers. Unless otherwise specified herein, the invention is intended to extend to each of these stereoisomeric forms and to mixtures thereof, including the racemates. In some cases there may be advantages, i.e. greater potency, to using a particular enantiomer when compared to the other enantiomer or the racemate in the methods of the instant invention and such advantages can be readily determined by those skilled in the art. The separate enantiomers may be synthesized from chiral starting materials or the racemates may be resolved by conventional procedures which are well known in the art of chemistry such as chiral chromatography, fractional crystallization of diastereomeric salts and the like. Likewise, the diastereomers can be separated by conventional procedures which are well known in the art of chemistry such as chromatography, fractional crystallization and the like.

Compounds of Formula I are believed to be useful both in the free base form and in the form of acid-addition salts, and, both forms are within the purview of the invention. The acid-addition salts are often a more convenient form for use; and in practice, use of the salt form inherently amounts to use of the base form. The acids that can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is believed to be convenient to use them in free base forms or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The suitably substituted 4-halo-1H-pyrazolo[3,4-b]quinolines of the formula II, which are required for the synthesis of the compounds of Formula I, can be prepared as shown in Scheme B:

Scheme B

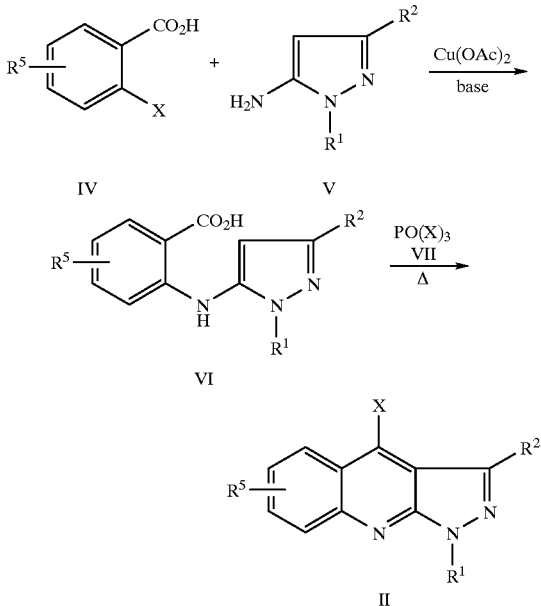

A suitably substituted benzoic acid derivative of Formula IV, wherein X is a halogen, preferably iodine, bromine or chlorine, in a suitable organic solvent, such as dimethylformnamide, is treated with at least one mole of a suitable base, such as potassium carbonate, at least one mole of a suitably substituted pyrazole derivative of Formula V and a catalytic amount of $Cu(OAc)_2$, at a temperature in the range of about room temperature up to the boiling point of the solvent used, preferably at the boiling point of the solvent used, to afford the suitably substituted anthranilic acid derivatives of Formula VI. The suitably substituted anthranilic acid derivative of Formula VI can then be treated with an excess of a phosporous oxyhalide of Formula VII, wherein X is a halogen, preferably chlorine, at a temperature in the range of about room temperature up to the boiling point of the reaction mixture, preferably at a temperature in the range of about 90° C. up to the boiling point of the reaction mixture, to afford the compounds of Formula II.

The suitably substituted amines of Formula III, the suitably substituted benzoic acid derivatives of Formula IV and the suitably substituted pyrazole derivatives of Formula V are either commercially available, or they can be prepared by procedures known in the art, or by the procedures described below in the examples which are provided in the aforesaid U.S. patent.

The structures of the compounds of the invention are established by the mode of synthesis, and by one or more of elemental analysis, and infrared, nuclear magnetic resonance and mass spectroscopy. The course of the reactions and the identity and homogenity of the products are assessed by one or more of thin layer chromatography (TLC), high pressure liquid chromatography (HPLC), or gas-liquid chromatography (GLC).

The following examples will further illustrate compounds useful in this invention without, however, limiting it. All melting points (m.p.) are given in degrees centigrade (° C.) and are uncorrected.

EXAMPLE 1

(a) To a solution of 2-iodobenzoic acid (54 g, 0.218 mol) in DMF (570 ml) is added potassium carbonate (33.4 g, 0.242 mol), followed by 5-amino-1-ethylpyrazole (24.2 g, 0.218 mol) and finally $Cu(OAc)_2.H_2O$ (0.9 g, 0.0045 mol). The reaction mixture is refluxed overnight, cooled and then poured into ice water. Acetic acid and HCl are added until a pH of about 4 is obtained. A precipitate forms which is collected by filtration, washed with water and dried to afford 21.4 g of N-(1-ethylpyrazol-5-yl) anthranilic acid.

(b) A mixture of N-(1-ethylpyrazol-5-yl)anthranilic acid (21.4 g, 0.0925 mol) and phosphorous oxychloride (312.8 g, 2.04 mol) is refluxed for 3 hours and then is stirred at room temperature overnight. The $POCl_3$ is removed by distillation, and the residue is poured into ice water. The solution is neutralized with 35% NaOH and extracted with $CH_2Cl_2$ (4x). The organic layer is separated, washed with water, then brine and then is dried over $MgSO_4$. The solvent is concentrated in vacuo and the residue is purified by column chromatography on silica gel eluting with $CH_2Cl_2$ to afford 17.5 g (81.7%) of 4-chloro-1-ethyl-1H-pyrazolo[3,4-b]quinoline. Alternatively, the reaction is run as described above, and then is worked up by neutralization with concentrated $NH_4OH$ to a pH of 8. Then the product, which crystallized directly from the solution, is collected by filtration.

(c) To a mixture of 4-chloro-1-ethyl-1H-pyrazolo[3,4-b]quinoline (10 g, 0.043 mol) and DMSO (75 ml) is added cyclohexanemethylamine (10.75 g, 0.095 mol). The reaction mixture is refluxed for about four hours, then is allowed to stand for about 2 days. About 40–50 ml of the DMSO is removed in vacuo and the residue is pured into ice waterl. A precipitate forms which is collected by filtration, washed with water and dried. The PG,13 solid precipitate is dissolved in $CH_2Cl_2$, washed with water, then brine and is then dried over $MgSO_4$. The solvent is filtered and concentrated in vacuo and the residue is purified by column chromatography on silica gel eluting with ethyl acetate/cyclohexane (3/7) followed by recrystallization from hexane to afford 12 g (90.2%) of 1-ethyl-N-(cyclohexylmethyl)-1H-pyrazolo[3,4-b]quinolin-4-amine, as light yellow crystals, m.p. 161°–163° C.

(d) 1-ethyl-N-(cyclohexylmethyl)-1H-pyrazolo[3,4-b]quinolin-4-amine is dissolved in warm methanol and treated with $CH_3SO_3H$. A solid forms which is collected by filtration and recrystallized from isopropanol/ether to afford 1-ethyl-N-(cyclohexylmethyl)-1H-pyrazolo[3,4-b]quinolin-4-amine. $CH_3SO_3H$, m.p. 215°–217° C.

EXAMPLE 2

(a) A mixture of 2-iodobenzoic acid (14.88 g, 0.06 mol), 1-ethyl-3-methyl-5-aminopyrazole (7.5 g, 0.06 mol), DMF (50 ml), Cu(OAc)2. $H_2O$ (0.5 g) and potassium carbonate (8.3 g, 0.06 mol) is refluxed for 20 hours. The reaction mixture is cooled to room temperature, poured into ice waterl and neutralized with acetic acid. A solid forms which is collected by filtration, washed with water and dried to give 7.1 g (98%) of N-(1-ethyl-3-methylpyrazol-5-yl) anthranilic acid.

(b) A mixture of N-(1-ethyl-3-methylpyrazol-5-yl) anthranilic acid (7.0 g), 28.57 mmol) and POCl3 (210 ml) is refluxed for 24 hours. The reaction mixture is cooled to room temperature, poured into ice waterl and neutralized with concentrated $NH_4OH$ to a pH of 8.0. The product which slowly crystallized from the solution is collected by filtration, washed with water and dried to afford 6.7 g (95%) of 4-chloro-1-ethyl-3-methyl-1H-pyrazolo[3,4-b]quinoline.

(c) A mixture of 4-chloro-1-ethyl-3-methyl-1H-pyrazolo[3,4-b]quinoline (1.0 g, 0.0043 mmol), cyclohexanemethylamine (1.2 ml, 0.009 mol) and DMSO (3 ml) is heated at 80° C. overnight. The reaction mixture is pured into water (100 ml)/NH₄OH (0.5 ml) and is extracted with CH₂Cl₂. The solvent is evaporated to about 20 ml and then the mixture is purified by chromatography on silica gel, followed by high pressure liquid chromatography eluting with 20% EtOAc/hexane to 50% EtOAc/hexane to afford the product as the free base. The free base is dissolved in CH₂Cl₂ (20 ml) and treated with ethereal HCl and the solution is evaporated. The residue is crystallized from ethyl acetate/ether/ethanol to afford 1-ethyl-3-methyl-N-(cyclohexylmethyl)-1H-pyrazolo[3,4-b]quinolin-4-amine hydrochloride, m.p. 215°–217° C.

EXAMPLE 3

A mixture of 4-chloro-1-ethyl-1H-pyrazolo[3,4-b]quinoline (3.0 g), trans-4-(aminomethyl)cyclohexane carboxylic acid (4.11 g) and DMSO (9 ml) is heated at 110°–120° C. overnight and then at reflux for 8 hours. The reaction mixture is cooled, partitioned between CH₂Cl₂ (100 ml)/ethanol (20 ml)/water (100 ml), and then the layers are separated. The organic layer is washed with water, dried over MgSO4, filtered and evaporated. The residue is passed through a silica gel column, and the filtrate is concentrated to afford an oil which is crystallized from hexane. The solid product is dissolved in methanol and treated with methanesulfonic acid, and then the methanol is removed. The residue is crystallized from 2-propanol and the product is collected by filtration, washed with ether and dried to afford 0.6 g of 1-ethyl-N-[(4-methoxycarbonylcyclohexyl)methyl]-1H-pyrazolo[3,4-b]quinolin-4-amine CH₃SO₃H, m.p. 232°–233° C.

EXAMPLE 4

Aminomethylcyclopropane hydrochloride (2.14 g, 0.02 mol) is treated with KOH/water/ether and then the ether layer is separated, and the ether is distilled off to afford aminomethyl cyclopropane as the free base which is then treated with 4-chloro-1-ethyl-1H-pyrazolo[3,4-b]quinoline (1.0 g, 0.0043 mol) and DMSO (3 ml). The mixture is stirred at 110° C. for about 4 days, cooled and partitioned between CH₂Cl₂ and water. The CH₂Cl₂ layer is concentrated and then the residue is purified by column chromatography on silica gel. The solid product is dissolved in methanol, treated with methanesulfonic acid and the methanol is removed. The residue is crystallized from 2-propanol and then recrystallized from 2-propanol to afford 1.0 g of 1-ethyl-N-(cyclopropylmethyl)-1H-pyrazolo[3,4-b]quinolin-4-amine, m.p. 228°–230° C.

EXAMPLE 5

A mixture of 4-chloro-1-ethyl-1H-pyrazolo[3,4-b]quinoline (3 g), DMSO (9 ml) and trans-4-(aminomethyl)cyclohexane carboxylic acid (4.1 g) is heated at 180° C. overnight. The reaction mixture is then partitioned between CH₂Cl₂ and water, the layers are separated and the aqueous layer is extracted with CH₂Cl₂. The organic layers are combined, washed with water, dried over Na₂SO₄, and evaporated. The residue is purified by column chromatography on silca gel to afford an oil which is crystallized from ether/hexane and then recrystallized from ether/hexane to afford 1-ethyl-N-[[4-(methylthiomethoxycarbonyl)cyclohexyl]methyl]-1H-pyrazolo[3,4-b]quinolin-4-amine, m.p. 135°–136° C.

EXAMPLE 6

(a) A mixture of 4-chloro-1-ethyl-1H-pyrazolo[3,4-b]quinoline (7 g, 0.03 mol), DMSO (20 ml) and trans-4-(aminomethyl) cyclohexane carboxylic acid is heated at 170°–180° C. for about 2 days. The reaction mixture is cooled, poured into 2N HCl (200 ml) and then is stirred for ½ hour and then allowed to stand for 2–3 hours. The solution is then poured into water, basified with NaOH and extracted with CH₂Cl₂ (2×50 ml). The aqueous layer is then brought to a pH of 5 and the water is decanted. The residual black gum that remained is dissolved in ethanol and cooled in an ice-bath. A solid forms which is collected by filtration and suspended in hot ethanol. The product is collected by filtration and dried to afford 1-ethyl-N-[(4-carboxycyclohexane)methyl]-1H-pyrazolo[3,4-b]quinolin-4-amine.

(b) A mixture of 1-ethyl-N-[(4-carboxycyclohexyl)methyl]-1H-pyrazolo[3,4-b]quinolin-4-amine (5.0 g), THF (100 ml) and lithium aluminum hydride (3.0 g) is refluxed overnight. Additional lithium aluminum hydride (1.0 g) is added, and the mixture is heated at reflux for another hour. The reaction mixture is cooled, water (4 ml), then 10% NaOH (4 ml) and finally water (12 ml) are added, and the mixture is heated to reflux and then filtered. The collected solids are heated at reflux in TBF for 10 minutes, then filtered again. The filtrates are combined, dried over MgSO₄ and then evaporated. The residue is purified by column chromatography on silica gel eluting with ethyl acetate and then is crystallized from hexanes/ethyl acetate. The product is dissolved in methanol, treated with methanesulfonic acid and then the methanol is evaporated. The residue is crystallized from 2-propanol and then recrystallized from 2-propanol to afford 1-ethyl-N-[(4-hydroxymethylcyclohexyl)methyl]-1H-pyrazolo[3,4-b]quinolin-4-amine.CH₃SO₃H, as a white solid, m.p. 188°–190° C.

EXAMPLE 7

(a) To m-anisic acid in acetic acid (1 L) is added dropwise bromine (85 ml), followed by water (1 L). The reaction mixture is heated to reflux, cooled in an ice-bath and then the product is collected by filtration, washed with cold water and dried to afford 2-bromo-5-methoxybenzoic acid, m.p. 154°–156° C.

(b) A mixture of 2-bromo-5-methoxybenzoic acid (39.3 g, 0.17 mol), DMF (150 ml), 5-amino-1-ethylpyrazole (18.5 g, 0.17 mol), potassium carbonate (23.5 g, 0.17 mol) and Cu(OAc)2 (0.6 g) is refluxed for about 2 days. The reaction mixture is cooled, poured into water and acidified to a pH of 5. A precipitate forms which is collected by filtration, washed with water and dried to afford 44.37 g (62%) of N-(1-ethylpyrazol-5-yl)-5-methoxyanthranilic acid.

(c) A mixture of N-(1-ethylpyrazol-5-yl)-5-methoxyanthranilic acid (27.5 g, 0.105 mol) and POCl3 (60 ml) is refluxed overnight. The reaction mixture is poured into ice waterl, basified with NH₄OH and the solid which forms is collected by filtration to afford 20 g of 4-chloro-1-ethyl-6-methoxy-1H-pyrazolo[3,4-b]quinoline.

(d) A mixture of 4-chloro-1-ethyl-6-methoxy-1H-pyrazolo[3,4-b]quinoline (7.83 g, 0.03 mol), cyclohexanemethylamine (7.8 ml, 0.06 mol) and DMSO is heated at 110° C. overnight. The reaction mixture is cooled, poured into water, and the solid that crystallizes is collected by filtration and dried to afford 6.6 g (66%) of the product as the free base. The free base (0.8 g) is converted into the methanesulfonic acid salt which is recrystallized from 2-propanol to afford 800 mg of 1-ethyl-6-methoxy-N-(cyclohexylmethyl)-1H-pyrazolo[3,4-b]quinolin-4-amine, m.p. 235°–237° C. Alternatively, the product can be isolated by pouring the reaction mixture into water, basifying with NH$_4$OH to a pH of about 8, extracting with CH$_2$Cl$_2$, drying the CH$_2$Cl$_2$ layer over MgSO$_4$ and evaporating the CH$_2$Cl$_2$; followed by purification of the residue by column chromatography on silica gel eluting with ethyl acetate.

EXAMPLE 8

A mixture of 1-ethyl-6-methoxy-N-(cyclohexylmethyl)-1H-pyrazolo[3,4-b]quinolin-4-amine (5.4 g, 0.016 mol), boron tribromide (48 ml, 0.048 mol) and 1,2-dichloroethane (250 ml) is stirred at room temperature overnight. The reaction mixture is stirred with 1 volume of water, made basic with NaOH, and the layers are separated. The basic layer is acidified with acetic acid and the yellow precipitate that forms is collected by filtration, washed with water and dried. The product is recrystallized from hot acetonitrile/methanol to afford 1-ethyl-6-hydroxy-N-(cyclohexylmethyl)-1H-pyrazolo[3,4-b]quinolin-4-amine, as a yellow powder, m.p. 223°–224° C.

EXAMPLE 9

(a) To a solution of acrylonitrile (122 ml, 2 mol) in ethanol (500 ml) in an ice-bath is added dropwise hydrazine hydrate (100 ml). The reaction mixture is stirred for 2 hours, then acetaldehyde (111.7 ml, 2.0 mol) is added and the mixture is stirred overnight. The ethanol is evaporated to afford NCCH$_2$CH$_2$NH—N═CH(CH$_3$), which is used directly in the next step.

(b) Sodium metal (50.6 g, 2.2 mol) is added to 1-butanol (2 L), and once all of the sodium metal dissolved the product of example 9(a) [NCCH$_2$CH$_2$NH—N═CH(CH$_3$)] is added and the reaction mixture is refluxed overnight. The excess butanol is evaporated, 1 volume of water is added and the layers are separated. The aqueous layer is washed with ether and the organic layers are combined, washed with brine and evaporated. The residue is vacuum distilled to afford 42 g of 5-amino-1-ethylpyrazole.

(c) A mixture of 3-methoxyanthranilic acid (16 g) and 10% sulfuric acid (250 ml) is warmed on a stream bath to effect a partial solution and then is rapidly cooled to 0°–3° C. and NaNO2 (7 g) in water (20 ml) is added dropwise. The reaction mixture is stirred for 30 minutes then potassium iodide (24 g) in water (40 ml) is added, and the mixture is allowed to warm 40°–50° C. over 3–4 hours and then is heated briefly at 60° C. The reaction mixture is extracted with ether, and the ether layer is washed with 5% NaOH. The aqueous layer is acidified with 2N HCl and extracted with ether. The ether is evaporated to afford 4 g of a mixture of 2-iodo-3-methoxybenzoic acid and 3-methoxybenzoic acid.

(d) A mixture of 5-amino-1-ethylpyrazole (1.6 g, 0.0144 mol), DMF (40 ml), potassium carbonate (2 g), Cu(OAc)2 (0.05 g), and 2-iodo-3-methoxybenzoic acid/3-methoxybenzoic acid (4 g) of example 9(c) is refluxed overnight. The reaction mixture is poured into water (200 ml) and acidified to pH 5 with acetic acid. The aqueous solution is extracted with ether (100–150 ml×5) and the aqueous layers are evaporated in vacuo. The residue from the aqueous layer is taken up in CH$_2$Cl$_2$ and filtered. The organic filtrate is combined with the ether layer above, and the mixture is evaporated in vacuo to afford 3–4 g of crude N-(1-ethylpyrazol-5-yl)-3-methoxy anthranilic acid, which is used directly in the next step.

(e) A mixture of N-(1-ethylpyrazol-5-yl)-3-methoxyanthranilic acid of example 9(d) and POCl3 (50 ml) is refluxed overnight. The reaction mixture is poured into ice waterl, neutralized with NH$_4$OH and the mixture is extracted with CH$_2$Cl$_2$ (3×150 ml). The CH$_2$Cl$_2$ extracts are combined, dried over MgSO$_4$, filtered and evaporated. The residue is purified by column chromatography on silica gel eluting with 35% EtOAc/hexane to afford 0.4 g of 4-chloro-1-ethyl-8-methoxy-1H-pyrazolo[3,4-b]quinoline, m.p. 168°–170° C.

(f) A mixture of 4-chloro-1-ethyl-8-methoxy-1H-pyrazolo[3,4-b]quinoline (0.4 g, 1.53 mmol), DMSO (1 ml) and cyclohexanemethylamine (0.4 ml, 3.06 mmol) is heated at 150° C. for 4 hours and then is stirred overnight at room temperature. The reaction mixture is partitioned between CH$_2$Cl$_2$ and water, a few drops of NH$_4$OH are added, and then the CH$_2$Cl$_2$ layer is evaporated to afford a residue that crystallizes from CH$_2$Cl$_2$ hexane. The solid product is treated with methanesulfonic acid and methanol, the methanol is evaporated and the residue is crystallized from 2propanol/ether and then recrystallized from 2-propanol/ether to afford 0.18 g of 1-ethyl-8methoxy-N-(cyclohexylfethyl)-1H-pyrazolo[3,4-b]quinolin-4-amine CH$_3$SO$_3$H, m.p. 222°–225° C.

EXAMPLE 10

(a) A mixture of acrylonitrile (15.3 g, 0.289 mol) and ethanol (75 ml) is stirred in an ice-bath and then hydrazine hydrate (15 ml, 0.3 mol) is added dropwise and the mixture is warmed to room temperature and stirred for 2 hours. Benzaldehyde (30.6 ml, 0.3 mol) is then added, and the reaction mixture is stirred at room temperature for about 2 days. The react on mixture is concentrated in vacuo and the residue is added to a solution of sodium butoxide in butanol [prepared from sodium metal (6.9 g) and butanol (300 ml)]. The reaction mixture is refluxed overnight, and then the solvent is concentrated in vacuo to afford 19.4 g of crude 5-amino-1-phenyl methylpyrazole.

(b) A mixture of 2-iodobenzoic acid (14 g, 0.057 mol), 5-amino-1-phenylmethylpyrazole (9.8 g, 0.057 mol), DMF (140 ml), potassium carbonate (8.3 g) and Cu(OAc)2 (0.1 g) is refluxed for about 2 days. The reaction mixture is poured into water, acidified with acetic acid to a pH of 5, and then the solid which forms is collected by filtration, washed with water, then ether and then is dried to afford N-(1-phenylmethylpyrazol-5-yl) anthranilic acid, m.p. 190° C.

(c) A mixture of N-(1-phenylmethylpyrazol-5-yl) anthranilic acid (6 g) and POCl3 (60 ml) is heated on a steam bath overnight. The reaction mixture is poured into ice waterl, neutralized with NH$_4$OH, and the precipitate which forms is collected by filtration, washed with water and dried to afford 5 g of 1-phenylmethyl-4-chloro-1H-pyrazolo[3,4-b]quinoline, as a light brown powder.

(d) A mixture of 1-phenylmethyl-4-chloro-1H-pyrazolo[3,4-b]quinoline (3.0 g, 10.2 mmol), DMSO (10 ml) and cyclohexanemethylamine (2.63 ml, 20.5 mmol) is heated at 110° C. for 4 hours and then is allowed to sit at room temperature overnight. The reaction mixture is partitioned between CH$_2$Cl$_2$/water and the organic layer is separated and evaporated. The residue is purified by column chromatography on silica gel eluting with 25% ethyl acetate/hexane to afford 2.5 g of the product as the free base. The free base (0.6 g) is treated with methanesulfonic acid/methanol to afford the CH$_3$SO$_3$H salt which is recrystallized from 2-propanol/ether to afford 1.22 g of 1-phenylmethyl-N-(cyclohexylmethyl)-1H-pyrazolo[3,4-b]quinolin-4-amine.CH$_3$SO$_3$H, as a beige solid, m.p. 254°–256° C.

EXAMPLE 11

(a) A mixture of acrylonitrile (17.4 ml, 0.264 mol), ethanol (160 ml) and hydrazine hydrate (13.2 ml, 0.264 mol)

are stirred for 2 hours and then cyclopentanone (24.8 ml, 0.28 mol) is added and the mixture is stirred overnight. The ethanol is evaporated to afford crude $NCCH_2CH_2NH-N=$cyclopentyl, which is used directly in the next step.

(b) A mixture of 1-butanol (400 ml) and sodium metal (6.5 g, 0.28 mol) is stirred until all of the sodium metal had dissolved and then the product of example 11(a) [$NCCH_2CH_2NH-N=$cyclopentyl] is added. The reaction mixture is refluxed overnight, the excess 1-butanol is evaporated and water is added. The water layer is separated and the residue is again treated with water. The water layers are combined and extracted with ether. The ether layer is washed with brine and then evaporated. The residue is purified by Kuglerohr distillation (2×) at 80°–120° C. and 1 mm Hg to afford 22.3 g of 5-amino-1-cyclopentylpyrazole, as a clear oil.

(c) A mixture of 2-iodobenzoic acid (28 g, 0.113 mol), 5-amino-1-cyclopentylpyrazole (17 g, 0.113 mol), DME (100 ml), potassium carbonate (16 g, 0.113 mol) and Cu(OAc)2 (0.5 g) is refluxed overnight. The reaction mixture is poured into ice water, and acidified with acetic acid to a pH of 5. The gum which forms is extracted with $CH_2Cl_2$ and the $CH_2Cl_2$ layer is washed with water, dried over $MgSO_4$, and evaporated to afford 21 g of N-(1-cyclopentyl pyrazol-5-yl) anthranilic acid.

(d) A mixture of N-(1-cyclopentylpyrazol-5-yl) anthranilic acid (21 g, 0.0775 mol) and $POCl_3$ (100 ml) is refluxed for 8 hours. The reaction mixture is poured into ice waterl and neutralized with $NH_4OH$. A gum forms which is extracted with $CH_2Cl_2$. The $CH_2Cl_2$ layer is then washed with water, dried over $MgSO_4$, filtered and concentrated. The residue is purified by column chromatography on silica gel eluting with 40% to 70% $CH_2Cl_2$/hexane to afford 7.5 g of 4-chloro-1-cyclopentyl-1H-pyrazolo[3,4-b]quinoline, m.p. 97°–98° C.

(e) A mixture of 4-chloro-1-cyclopentyl-1H-pyrazolo[3,4-b]quinoline (1 g, 0.0037 mol), DMSO (2 ml) and cyclohexanemethylamine (0.96 ml, 0.0075 mol) is heated at 110° C. for 4 hours and then is allowed to stand overnight. The reaction mixture is partitioned between water/$CH_2Cl_2$, and the $CH_2Cl_2$ layer is separated and evaporated. The residue is purified by column chromatography on silca gel eluting with 25% ethyl acetate/hexane to afford 1.2 g of the product as the free base. The free base is treated with methanesulfonic acid/methanol, and the methanesulfonic acid salt is crystallized from 2-propanol/ether to afford 722 mg of 1-cyclopentyl-N-(cyclohexylmethyl)-1H-pyrazolo[3,4-b]quinolin-4-amine, m.p. 290°–292° C.

EXAMPLE 12

A mixture of 1-ethyl-6-hydroxy-N-(cyclohexylmethyl)-1H-pyrazolo[3,4-b]quinolin-4-amine (2 g, 0.0062 mol), KOH (2 g), DMSO (35 ml) and dimethylaminoethyl chloride (0.7 g, 0.0065 mol) is stirred at room temperature for 4 hours and then is allowed to stand overnight. The reaction mixture is partitioned between $CH_2Cl_2$ (75 ml) and water (75 ml), the layers are separated and the aqueous layer is extracted with $CH_2Cl_2$ (2×). The $CH_2Cl_2$ layers are combined, dried over $K_2CO_3$ and evaporated. The residue is purified by column chromatography on silica gel eluting with 50% ether/methanol, followed by a second column chromatography eluting with 25% methanol/ether to afford the product as the free base. The free base is taken up in methanol, treated with methanesulfonic acid, and the methanol is evaporated. The residue is crystallized from hot 2-propanol/ether and then is recrystallized from hot 2-propanol/ether to afford 696 mg of 1-ethyl-6-[2-(dimethylamino)ethoxyl-N-(cyclohexymethyl)-1H-pyrazolo[3,4-b]quinolin-4-amine.2-$CH_3SO_3H$, m.p. 186°–188° C.

EXAMPLE 13

A mixture of 1-ethyl-6-hydroxy-N-(cyclohexymethyl)-1H-pyrazolo[3,4-b]quinolin-4-amine (2.0 g, 6.2 mmol), DMSO (30 ml), ethylbromoacetate (0.67 ml, 6 mmol) and KOH (2 g) is stirred at room temperature overnight. The reaction mixture is poured into water and acidified with acetic acid to a pH of about 5. A solid forms which is collected by filtration, washed with water and then stirred with hot ethyl acetate/$CH_2Cl_2$. The mixture is filtered and washed with ether to afford 1.5 g of 1-ethyl-6-(carboxymethoxy)-N-(cyclohexymethyl)-1H-pyrazolo[3,4-b]quinolin-4-amine. ¾ hydrate, m.p. 280° C. (dec.).

EXAMPLE 14

A mixture of 4-chloro-1-ethyl-1H-pyrazolo[3,4-b] quinoline (1 g), DMSO (3 ml) and adamantylmethylamine (1 g) is heated at 110° C. overnight. The reaction mixture is poured into water, and a precipitate forms which is collected by filtration and dried to afford the product as a free base. The free base is treated with methanesulfonic acid/methanol, the methanol is evaporated and the salt is recrystallized from 2-propanol to afford 290 mg of 1-ethyl-N-(adamantylmethyl)-1H-pyrazolo[3,4-b]quinolin-4-amine.$CH_3SO_3H$, m.p. 310° C.

EXAMPLE 15

(a) A mixture of 2-chloro-5-nitrobenzoic acid (4.03 g, 0.02 mol), 5-amino-1-ethylpyrazole (2.22 g, 0.02 mol), DMF (25 ml), $K_2CO_3$ (2.76 g, 0.02 mol) and Cu(OAc)$_2$H$_2$O (0.5 g) is refluxed for 24 hours. The reaction mixture is cooled to room temperature, poured into ice waterl and acidified with acetic acid to a pH of 5. A solid forms which is collected by filtration and dried to afford 3.8 g (68%) of N-(1-ethylpyrazol-5-yl)-5-nitroanthranilic acid.

(b) A mixture of N-(1-ethylpyrazol-5-yl)-5-nitroanthranilic acid (3.8 g, 13.77 mmol) and $POCl_3$ (20 ml) is refluxed for 8 hours. The reaction mixture is poured into ice waterl, neutralized with concentrated $NH_4OH$, and the resulting solid is collected by filtration, washed with water and dried to afford 2.5 g (65%) of 1-ethyl-4-chloro-6-nitro-1H-pyrazolo[3,4-b]quinoline.

(c) A mixture of 1-ethyl-4-chloro-6-nitro-1H-pyrazolo[3,4-b]quinoline (2.2 g, 7.95 mmol), DMSO (10 ml) and cyclohexanemethylamine (1.8 g, 16 mmol) is heated at 120°–130° C. for 18 hours. The reaction mixture is cooled to room temperature, and poured into ice water. A solid forms which is collected by filtration and dried to afford 2.9 g of the product as the free base. The free base (0.6 g) is dissolved in hot methanol, cooled to room temperature and then treated with one equivalent of methanesulfonic acid. Ether is added to the mixture and the solid which forms is collected by filtration and recrystallized from methanol/ether, to afford 0.5 g of 1-ethyl-6-nitro-N-(cyclohexylmethyl)-1H-pyrazolo[3,4-b]quinolin-4-amine.$CH_3SO_3H$, m.p. 261°–263° (dec.).

EXAMPLE 16

(a) A mixture of 2-chloro-4-nitrobenzoic acid (4.03 g, 0.02 mol), 5-amino-1-ethylpyrazole (2.22 g, 0.02 mol), DMF (25 ml), $K_2CO_3$ (2.76 g, 0.02 mol) and Cu(OAc)2.

$H_2O$ (0.5 g) is refluxed for 24 hours. The reaction mixture is cooled to room temperature, poured into ice water and then acidified with acetic acid to a pH of 5. A solid forms which is collected by filtration and dried to afford 3.5 g (63%) of N-(1-ethylpyrazol-5-yl)-4-nitroanthranilic acid.

(b) A mixture of N-(1-ethylpyrazol-5-yl)-4-nitroanthranilic acid (3.4 g, 12.32 mmol) and $POCl_3$ (20 ml) is refluxed for 8 hours. The reaction mixture is poured into ice waterl, neutralized with concentrated $NH_4OH$, and the resulting solid is collected by filtration,washed with water and dried to afford 2.8 g (82%) of 1-ethyl-4-chloro-7-nitro-1H-pyrazolo[3,4-b]quinoline.

(c) A mixture of 1-ethyl-4-chloro-7-nitro-1H-pyrazolo[3,4b]quinoline (2.5 g, 9.04 mmol), DMSO (10 ml) and cyclohexanemethylamine (2.05 g, 18.1 mmol) is heated at 120°–130° C. for 18 hours. The reaction mixture is cooled to room temperature, poured into ice wafer, and the resulting solid is collected by filtration and dried to afford 3.0 g of crude product. The product is purified by column chromatography on silica gel eluting with CH2Cl2 ether (4/1) to afford 2.2 g (69%) of 1-ethyl-7-nitro-N-(cyclohexylmethyl)-1H-pyrazolo[3,4-b]quinolin-4-amine, m.p. 205°–207° C.

EXAMPLE 17

(a) A mixture of 1-ethyl-6-hydroxy-N-(cyclohexylmethyl)-1H-pyrazolo[3,4-b]quinolin-4-amine (6 g), KOH (5 g), and DMSO (70 ml) is stirred for 30 minutes and then epichlorohydrin (1.5 ml) is added. The reaction mixture is stirred overnight and then is partitioned between $CH_2Cl_2$ and water. The organic layer is then separated, dried and evaporated to dryness. The residue is purified by column chromatography on silica gel eluting with ethyl acetate, followed by crystallization from hexane/ether to afford 1.0 g of 1-ethyl-6-(2,3-epoxypropoxy)-N-(cyclohexylmethyl)-1H-pyrazolo[3,4-b]quinolin-4-amine, m.p. 160°–163° C.

(b) A mixture of 1-ethyl-6-(2,3-epoxypropoxy)-N-(cyclohexylmethyl)-1H-pyrazolo[3,4-b]quinolin-4-amine (0.53 g) and formic acid (10 ml) are stirred at room temperature overnight. The excess formic acid is removed in vacuo and then methanol (75 ml) and triethylamine (10 ml) are added, and the mixture is stirred for four hours. The reaction mixture is evaporated, ether is added, and the product which crystallizes is recrystallized from $CH_2Cl_2$/$Et_2O$ and then purified by column chromatography on silca eluting with $CH_2Cl_2$/THF (1/1) to afford 1-ethyl-6-(2,3-dihydroxypropoxy)-N-(cyclohexylmethyl)-1H-pyrazolo[3,4-b]quinolin-4-amine, m.p. 197°–199° C.

EXAMPLE 18

(a) A mixture of 2-nitro-4-methoxybenzoic acid (21.9 g, 0.111 mol), 2N ammonium hydroxide (250 ml) and 5% palladium on strontium carbonate (2.5 g) is shaken under 45 psi of hydrogen pressure for 3–4 hours. The reaction mixture is filtered, and the filtrate is acidified with acetic acid. A solid forms which is collected by filtration, washed with water and dried to afford 16 g of 4-methoxyanthranilic acid, m.p. 194°–195° C.

(b) To a mixture of 50% sulfuric acid (150 ml) and 4-methoxyanthranilic acid (12 g) at 5°–10° C. is added sodium nitrite (5.5 g) in water, followed 10 minutes later by NaI (16.5 g) in water (30–50 ml). The reaction mixture is warmed to room temperature and stirred for 2 hours, then is heated at 60°–70° C. for 10 minutes, followed by stirring at room temperature for 1 hour. The reaction mixture is extracted with ether (4×125 ml) and the combined ether extracts are washed with water (50 ml×2), dried over $MgSO_4$, filtered and evaporated. The residue is purified by column chromatography on silica gel eluting with ether to afford 12 g of 2-iodo-4-methoxybenzoic acid.

(c) A mixture of 2-iodo-4-methoxybenzoic acid (13.6 g, 48.9 mmol), 5-amino-1-ethylpyrazole (5.5 g, 49 mmol), DMF (100 ml), $K_2CO_3$ (6.9 g, 0.05 mol) and Cu(OAc)2 (0.5 g) is refluxed overnight. The reaction mixture is poured into water (500 ml) and acidified with acetic acid to a pH of 5–6. The product slowly crystallized from the solution and is collected by filtration and washed with water. The solid is taken up in $CH_2Cl_2$/methanol, dried, filtered and evaporated. The residue is combined with $POCl_3$ (60 ml) and refluxed overnight. The reaction mixture is cooled, poured into water and neutralized with concentrated $NH_4OH$. The mixture is extracted with $CH_2Cl_2$, and the $CH_2Cl_2$ extracts are evaporated, and the residue is purified by column chromatography on silica gel eluting with ethyl acetate to afford 5 g of 1-ethyl-4-chloro-7-methoxy-1H-pyrazolo[3,4-b]quinoline, m.p. 114°–115° C.

(d) A mixture of 1-ethyl-4-chloro-7-methoxy-1H-pyrazolo[3,4-b]quinoline (4.0 g, 15.3 mmol), cyclohexanemethylamine (3.74 g, 33 mmol) and DMSO (12 ml) is heated at 110° C. overnight. The reaction mixture is poured into water (200 ml) and the solid which forms is collected by filtration. The filtrate is extracted with $CH_2Cl_2$ (40 ml) and the solid is added to the $CH_2Cl_2$ and the solution is dried over $MgSO_4$. The $CH_2Cl_2$ is evaporated to 20–30 ml and then is passed through a silica gel column eluting with ethyl acetate to afford 4 g of the product as the free base. The free base is treated with methanesulfonic acid/methanol to afford 1-ethyl-7-methoxy-N-(cyclohexylmethyl)-1H-pyrazolo[3,4-b]quinolin-4-amine. $CH_3SO_3H$.

EXAMPLE 19

(a) To a solution of benzylamine (12.8 g, 0.12 mol) in toluene (120 ml) at 0° C. is added trimethyl aluminum (60 ml, 0.12 mol, 2M in toluene). The reaction mixture is stirred at room temperature for 1 hour, then is cooled to 0° C. and then ethyl 4-hydroxycylcohexylcarboxylate (10.32 g, 0.06 mol) in toluene (250 ml) is added and the reaction mixture is stirred for about 2 days. The reaction mixture is poured into ice water containing 2N HCl (300 ml) and is stirred for 30 minutes. The organic layer is separated, the aqueous layer is extracted with ethyl acetate (2×150 ml), and the combined organic layers are washed with brine and dried over $MgSO_4$. Removal of the solvent and tituration with hexane afforded 9.1 g (64%) of N-benzyl-4-hydroxcyclohexylamide.

(b) To a solution of N-benzyl-4-hydroxycyclohexylamide (9 g, 38.62 mmol) in THF (250 ml) is added lithium aluminum hydride (4.74 g, 125 mmol). The reaction mixture is stirred at room temperature for 30 minutes, then is relfuxed for 18 hours. The reaction mixture is cooled in an ice-bath, neutralized with saturated $Na_2SO_4$, and then filtered. The filtrate is evaporated to dryness to afford 8.5 g of N-benzyl-N-(4-hydroxycyclohexylmethyl) amine.

(c) To a stirred solution of N-benzyl-N-(4-hydroxycyclohexyl methyl)amine (8.5 g, 0.039 mol) in methanol (300 ml) under N2 is added ammonium formate (9.8 g, 0.0155 mol), followed by 10% palladium on carbon (1.0 g). The reaction mixture is refluxed for 3 hours, cooled to room temperature and filtered. The filtrate is evaporated to dryness and the residue is dissolved in $CH_2Cl_2$, filtered and the filtrate is evaporated to afford 1.3 g of 4-hydroxycyclohexylmethylamine.

(d) A mixture of 4-hydroxycyclohexylmethylamine (2.2 g, 17.05 mmol), 1-ethyl-4-chloro-6-methoxy-1H-pyrazolo

[3,4-b]quinoline (2.0 g, 7.66 mmol) and DMSO is heated at 110°–120° C. under a nitrogen atmosphere for 16 hours. The reaction mixture is poured into ice water, and the mixture is extracted with $CH_2Cl_2$ (4×50 ml). The organic layers are combined, dried over $MgSO_4$ and evaporated to dryness. The residue is purified by column chromatography on silica gel eluting with $CH_2Cl_2$/methanol (9/1), followed by a second silica gel column eluting with ethyl acetate to afford 1.3 g of crude product. The crude product is dissolved in warm methanol, cooled to room temperature and treated with an equivalent amount of methanesuflonic acid. Ether is added to the mixture and the solid which forms is collected by filtration, washed with ether and recrystallized from isopropanol to afford 0.85 g of 1-ethyl-6-methoxy-N-(4-hydroxycyclohexylmethyl)-1H-pyrazolo[3,4-b]quinolin-4-amine. $CH_3SO_3H$, as yellow crystals, m.p. 256°–258° C. (dec.)

EXAMPLE 20

A mixture of 1-ethyl-6-nitro-N-(cyclohexylmethyl)-1H-pyrazolo[3,4-b]quinolin-4-amine (2.3 g, 6.51 mmol), methanol (20 ml), 10% palladium on carbon (0.3 g) and ammonium formate (1.9 g, 30 mmol) is stirred at room temperature under argon for 2 hours and then is heated on a steam bath for 3 hours. The reaction mixture is filtered, the filter cake is washed with methanol and the filtrate is evaporated to dryness. The residue is partitioned between $CH_2Cl_2$ and water, and the organic layer is separated, dried over $MgSO_4$ and evaporated to dryness. The residue is purified by column chromatography on silica gel eluting with $CH_2Cl_2$/ MeOH (9/1) to afford 1.0 g (45%) of the product as the free base. The free base is dissolved in methanol and treated with one equivalent of methanesulfonic acid. Ether is added to the mixture and the resulting solid is collected by filtration and recrystallized from $CH_2Cl_2$/ether to afford 0.77 g of 1-ethyl-6-arnino-N-(cyclohexylmethyl)-1H-pyrazolo[3,4-b] quinolin-4-amine.$CH_3SO_3H$, m.p. 232°–234° C. (dec.).

EXAMPLE 21

A mixture of 1-ethyl-6-hydroxy-N-(cyclohexylmethyl)-1H-pyrazolo[3,4-b]quinolin-4-amine (2 g), DMSO (30 ml) and KOH (2 g) is stirred at room temperature for 0.5 hours, then epichlorohydrin (0.49 ml) is added, and the mixture is stirred overnight. The reaction mixture is partitioned between $CH_2Cl_2$ and water, and then the $CH_2Cl_2$ layer is separated and evaporated. The residue is purified by column chromatography on silica gel eluting with ethyl acetate to afford the product that is combined with the product from a similar experimental. The combined material is purified further by column chromatography on silica gel eluting with 90% ether/t-butylmethylether, followed by crystallization from ether, to afford 1-ethyl-6-(2,3-epoxypropoxy)-N-(cyclohexylmethyl)-1H-pyrazolo[3,4-b]quinolin-4amine, m.p. 168°–170° C.

EXAMPLE 22

A mixture of 1-ethyl-6-hydroxy-N-(cyclohexylmethyl)-1H-pyrazolo[3,4-b]quinolin-4-amine (0.5 g, 1.5 mmol), DMSO (5 ml) and KOH (0.5 g) is stirred at room temperature for 20 minutes, then ethyl 2-bromopropionate (0.2 ml) is added, and the mixture is stirred overnight. The reaction mixture is poured into 10 volumes of water, extracted with $CH_2Cl_2$ (2×10 ml), and the aqueous layer is acidified with acetic acid. A precipitate forms which is collected by filtration, dissolved in methanol and filtered. The filtrate is allowed to stand, and the product that precipitates is collected by filtration and dried to afford 180 mg of 1-ethyl-6-(1-carboxyethoxy)-N-(cyclohexylmethyl)-1H-pyrazolo[3,4-b]quinolin-4-amine. ¼ Hydrate, m.p. 280° C. (dec.).

EXAMPLE 23

(a) A mixture of 2-bromoterephthalic acid (4.8 g, 0.02 mol), DME (50 ml), Cu(OAc)2 (0.2 g), 5-amino-1-ethylpyrazole (2.22 g, 0.02 mol) and $K_2CO_3$ (2.71 g, 0.02 mol) is heated at 135° C. overnight, then at reflux overnight. The reaction mixture is poured into water, acidified with acetic acid and the precipitate which forms is collected by filtration and dried to afford 2.5 g of N-(1-ethylpyrazol-5-yl)-4-carboxyanthranilic acid.

(b) A mixture of N-(1-ethylpyrazol-5-yl)-4-carboxyanthranilic acid (2.5 g) and POCl3 (20 ml) is refluxed overnight. The reaction mixture is poured into water, acidified with acetic acid, and the solids which form are collected by filtration. The solid is taken up in 10% NaOH, washed with ether and then the aqueous layer is acidified with concentrated HCl. The mixture is extracted with ether, the ether layer is dried over $MgSO_4$ filtered and evaporated to afford 1 g of 1-ethyl-4-chloro-7-carboxy-1H-pyrazolo[3,4-b]quinoline, as a yellow powder.

(c) A mixture of 1-ethyl-4-chloro-7-carboxy-1H-pyrazolo[3,4-b]quinoline (0.9 g, 3.3 mmol), DMSO (9 ml) and cyclohexanemethyl amine (0.86 ml, 6.6 mmol) is heated at 120°–130° C. for 6 hours. The reaction mixture is poured into water, acidified with acetic acid and the solid which forms is collected by filtration, dissolved in 5% NaOH and extracted with $CH_2Cl_2$ (2×50 ml). The aqueous layer is acidified with acetic acid and the solid that forms is collected by filtration and washed with water. The solid is purified by column chromatography on silica gel eluting with 30% methanol/10% acetic acid/60% $CH_2Cl_2$ to afford 1-ethyl-7-carboxy-N-(cyclohexylmethyl)-1H-pyrazolo[3,4-b] quinolin-4-amine, as a yellow solid.

EXAMPLE 24

(a) A mixture of 5-acetamido-2-bromobenzoic acid (7 g, 27 mmol), DMF (25 ml), Cu(OAc)2 (0.2 g), 5-amino-1-ethyl-pyrazole (3 g, 27 mmol) and $K_2CO_3$ (3.7 g, 27 mm is refluxed for about 2 days. The reaction mixture is poured into water, acidified with acetic acid and cooled. A solid forms which is collected by filtration to afford 2 g of N-(1-ethylpyrazole-5-yl)-5-acetamidoanthranilic acid.

(b) A mixture of N-(1-ethylpyrazole-5-yl)-5-acetamido anthranilic acid (2 g) and $POCl_3$ (20 ml) is refluxed overnight. The reaction mixture is poured into ice water (400 ml), neutralized with $NH_4OH$ and extracted with $CH_2Cl_2$ (3×100 ml). The $CH_2Cl_2$ layers are combined and concentrated in vacuo, and the residue is purified by column chromatography on silica gel eluting with ethyl acetate to afford 0.2 g of 1-ethyl-4-chloro-6-acetamido-1H-pyrazolo [3,4-b]quinoline.

(c) A mixture of 1-ethyl-4-chloro-6-acetamido-1H-pyrazolo[3,4-b]quinoline (0.2 g, 0.7 mmol), cyclohexanem-ethylamirie (0.5 ml, 3.5 mmol) and DMSO (3 ml) is heated at 110° C. for 6 hours. The reaction mixture is poured into water (50 ml), extracted with $CH_2Cl_2$ (4×25 ml), and the organic layers are combined and evaporated. The residue is slurried in ether, and a yellow solid is collected by filtration and recrystallized from ethanol/ethyl acetate to afford 200 mg of 1-ethyl-6-acetamido-N-(cyclohexylmethyl)-1H-pyrazolo[3,4-b]quinolin-4-amine, m.p. 277°–278° C.

EXAMPLE 25

A mixture of 1-ethyl-7-nitro-N-(cyclohexylmethyl)-1H-pyrazolo[3,4-b]quinolin-4-amine (1.6 g, 4.53 mmol), methanol (150 ml), 10% palladium on carbon (100 mg) and $CHCl_3$ (1 ml) is hydrogenated on a Parr apparatus at 40 psi for 8 hours. The catalyst is removed by filtration, and the filtrate is concentrated in vacuo. The residue is treated with concentrated $NH_4OH$ and extracted with $CH_2Cl_2$ (2×50 ml). The $CH_2Cl_2$ layers are combined, dried over $MgSO_4$ and evaporated. The residue is dissolved in warm methanol, and an equivalent amount of methanesulfonic acid is added. A solid forms which is collected by filtration and recrystallized from $CH_2Cl_2$/ether to afford 0.8 g of crude product. The crude product is dissolved in $CH_2Cl_2$, treated with $NH_4OH$ and then the $CH_2Cl_2$ is evaporated to afford the product as the free base. The free base is purified by column chromatography on silica gel eluting with $CH_2Cl_2$/methanol (4/1) to afford 0.4 g of the purified free base, which is dissolved in methanol and treated with methanesulfonic acid to afford the methanesulfonic acid salt. The salt is recrystallized from isopropanol to afford 0.28 g of 1-ethyl-7-amino-N-(cyclohexylmethyl)-1H-pyrazolo[3,4-b]quinolin-4-amine.$CH_3SO_3H$. ¼ $H_2O$, m.p. 268°–270° C. (dec.).

EXAMPLE 26

A mixture of S(+)-1-cyclohexylethylamine (0.734 ml), 1-ethyl-4-chloro-6-methoxy-1H-pyrazolo[3,4-b]quinoline (1.3 g, 5 mmol), DMSO (3 ml) and triethylamine (1.5 ml, 0.01 mol) is heated at 110° C. overnight. The reaction mixture is partitioned between $CH_2Cl_2$ and water and the $CH_2Cl_2$ layer is separated and evaporated to dryness. The residue is purified by column chromatography on silica gel eluting with 60% ethyl acetate/hexane to afford 0.4 g of the product as the free base. The free base is treated with ethanol/methanesulfonic acid to afford 0.251 g of 1-ethyl-6-methoxy-N-[S(+)-1-(cyclohexyl)ethyl]-1H-pyrazolo[3,4-b]quinolin-4-amine.$CH_3SO_3H$. ½ $H_2O$, m.p. 159°–160° C., [alpha]<25>D=71.6°. $CHCl_3$.

EXAMPLE 27

A mixture of R (−)-1-cyclohexylethylamine (0.734 ml). 1-ethyl-4-chloro-6-methoxy-1H-pyrazolo[3,4-b]quinoline (1.3 g, 5 mmol), DMSO (3 ml) and triethylamine (1.5 ml, 0.01 mol) is heated at 110° C. overnight. The reaction mixture is partitioned between $CH_2Cl_2$ and water and the $CH_2Cl_2$ layer is separated and evaporated. The residue is purified by column chromatography on silica gel (2×) eluting with 60% ethyl acetate/hexane to afford the product as the free base. The free base is treated with methanol/methanesulfonic acid, and the salt is crystallized from 2-propanol/ether to afford 0.4 g of 1-ethyl-6-methoxy-N-[R (−)-1-(cyclohexyl)ethyl]-1H-pyrazolo[3,4-b]quinolin-4-amine. $CH_3SO_3H$. ½ $H_2O$, m.p. 154°–160° C., [alpha] 25D=−74.9°, $CHCl_3$.

EXAMPLE 28

(a) A mixture of 1-ethyl-4-chloro-6-methoxy-1H-pyrazolo[3,4-b]quinoline (2.02 g, 15.5 mmol), DMSO (6 ml) and 4-hydroxy cyclohexylmethylamine (2 g, 15.5 mmol) is heated at 110° C. overnight. The reaction mixture is partitioned between $CH_2Cl_2$/water/$NaHCO_3$, and the $CH_2Cl_2$ layer is separated, dried over $MgSO_4$ and evaporated. The residue is purified by column chromatography on silica gel eluting with ethyl acetate to afford 1.8 g of 1-ethyl-6-methoxy-N-(4-hydroxycyclohexylmethyl)-1H-pyrazolo[3,4-b]quinolin-4-amine.

(b) To a solution of $CH_2Cl_2$ (35 ml) and trifluoroacetic anhydride (3.6 ml, 0.0224 mol) at −78° C. is added $CH_2Cl_2$ (5 ml) and DMSO (3.22 ml, 0.0454 mol). The reaction mixture is stirred for 1 hour, then a solution of 1-ethyl-6-methoxy-N-(4-hydroxycyclohexylmethyl)-1H-pyrazolo-[3,4-b]quinolin-4-amine (1.8 g, 0.0051 mol) in $CH_2Cl_2$ (30 ml) is added, and the reaction mixture is slowly warmed to 0° C. with stirring overnight. The reaction mixture is cooled to −78° C. and triethylamine (11 ml, 0.075 mol) is added. The reaction mixture is warmed to room temperature, stirred for 5 hours and then poured into water. The mixture is extracted with $CH_2Cl_2$ and the $CH_2Cl_2$ extracts are combined, washed with water, dried over $MgSO_4$ and evaporated. The residue is purified by column chromatography on silica gel eluting with ethyl acetate to afford the product as the free base. The free base is dissolved in 2-propanol and methanesulfonic acid is added. The volume is reduced to about 5 ml, ether is added and the precipitated salt is collected by filtration and recrystallized from 2-propanol/ether to afford 1 g of 1-ethyl-6-methoxy-N-[4-oxocyclohexylmethyl]-1H-pyrazolo[3,4-b]quinolin-4-amine. $CH_3SO_3H$. ½ $H_2O$.

EXAMPLE 29

(a) A mixture of 2,5-dibromobenzoic acid (25 g, 0.09 mol), DMF (200 ml), 5-amino-1-ethylpyrazole (10 g, 0.09 mol), Cu(OAc)$_2$ (1 g) and $K_2CO_3$ (12.3 g, 0.09 mol) is heated at reflux for about 2 days. The reaction mixture is poured into water, acidified with acetic acid, and the precipitate which forms is collected by filtration to afford 12.6 g of N-(1-ethylpyrazol-5-yl)-5-bromoanthranilic acid.

(b) A mixture of N-(1-ethylpyrazol-5-yl)-5-bromoanthranilic acid (12.6 g) and $POCl_3$ (30 ml) is refluxed overnight. The reaction mixture is poured into ice water (500 ml), stirred for 20 minutes, and then $NH_4OH$ is added until a pH of 8–10 is obtained. The mixture is stirred for 0.5 hours, and then the solid that forms is collected by filtration. The solid is dissolved in $CH_2Cl_2$, dried over $MgSO_4$ and purified by column chromatography on silica gel eluting with 30% hexane/ethyl acetate to afford 6.5 g of 1-ethyl-4-chloro-6-bromo-1H-pyrazolo[3,4-b]quinoline, m.p. 117°–118° C.

(c) A mixture of 1-ethyl-4-chloro-6-bromo-1H-pyrazolo [3,4-b]quinoline (6.5 g, 0.021 mol), cyclohexanemethylamine (5.46 g, 0.042 mol) and DMSO (20 ml) is heated at 110° C. overnight. The reaction mixture is cooled, poured into water and basified with $NH_4OH$. The mixture is extracted with $CH_2Cl_2$ (2×100 ml), and the combined $CH_2Cl_2$ extracts are washed with brine, then evaporated to about 20 ml. The solution is purified by column chromatography on silica gel eluting with ethyl acetate to afford 8.0 g (98.8%) of 1-ethyl-6-bromo-N-(cyclohexylmethyl)-1H-pyrazolo[3,4-b]quinolin-4-amine, m.p. 158°–160° C.

(d) Carbon monoxide is bubbled into a solution of bis (triphenylphosphine) palladium II chloride (0.07 g, 0.1 mol), methanol (100 ml), triphenylphosphine (0.13 g, 0.5 mmol), sodium acetate (0.9 g, 11 mmol), 1-ethyl-6-bromo-N-(cyclohexylmethyl)-1H-pyrazolo[3,4-b]quinolin-4-amine (4 g, 10.3 mmol) and triethylamine (0.138 ml, 1 mmol) overnight while the solution is heated at 60°–70° C. Additional bis(triphenylphosphine) palladium II chloride (0.07 g) is added, and the mixture is heated until the reaction is complete. The catalyst is removed by filtration, the filtrate is evaporated and the residue is partitioned between $CH_2Cl_2$/water. The $CH_2Cl_2$ layer is separated and evaporated to afford 2.2 g of the free base, m.p. 115°–118° C. The free base (0.7 g) is dissolved in $CH_3CN$ and treated with 2N HCl. The salt which forms is collected by filtration and washed with ether to afford 0.47 g of 1-ethyl-6-methoxycarbonyl-N-(cyclohexylmethyl)-1H-pyrazolo[3,4-b]quinolin-4-amine.HCl, m.p. 275°–277° C.

23

EXAMPLE 30

A mixture of 1-ethyl-6-methoxycarbonyl-N-(cyclohexylmethyl)-1H-pyrazolo[3,4-b]quinoline-4-amine (1.4 g), ethanol (90 ml), KOH (2 g) and water (10 ml) is stirred at room temperature overnight. The reaction mixture is evaporated and the residue is partitioned between $CH_2Cl_2$ and water. The aqueous layer is separated, acidified with acetic acid and the solid that forms is collected by filtration and dried. The solid is recrystallized from hot acetic acid (50 ml) to afford 1.0 g of 1-ethyl-6-carboxy-N-(cyclohexylmethyl)-1H-pyrazolo[3,4-b]quinolin-4-amine. HOAc, m.p. 240° C.

EXAMPLE 31

A mixture 1-ethyl-6-bromo-N-(cyclohexylmethyl)-1H-pyrazolo[3,4-b]quinolin-4-amine (2.0 g, 5.17 mmol), DMF (20 ml), bis(triphenylphospine)palladium II chloride (0.05 g) and tri-n-butyl-4-pyridyl stannane (2 g, 5.17 mmol) overnight, then at reflux overnight. The reaction mixture is poured into water and extracted with $CH_2Cl_2$ (3×30 ml). The $CH_2Cl_2$ extracts are combined, washed with water, dried over $Na_2SO_4$ and evaporated. The residue is purified by column chromatography on silica gel eluting with 20% ethyl acetate/hexane to 100% ethyl acetate to afford 1 g of the product as the free base. The free base is dissolved in $CH_2Cl_2$ (40–50 ml) and then is treated with methanesulfonic acid (20–30 ml). Ether is added to the mixture, and the precipitate that forms is collected by filtration and washed with $CH_2Cl_2$ (10 ml). The solid is recrystallized from hot 2-propanol/methanol to afford 0.85 g of 1-ethyl-6-(4-pyridinyl-N-(cyclohexylmethyl)-1H-pyrazolo[3,4-b]quinolin-4-amine.2 $CH_3SO_3H$.⅙ 2-propanol, m.p. 285° C.

EXAMPLE 32

1-Aminomethyl-1-cyclohexanol hydrochloride (1 g, 6.04 mmol) is dissolved in cold water and then $K_2CO_3$ and ether are added. The mixture is stirred, and then the ether layer is separated and the aqueous layer is again extracted with ether. The ether layers are combined, dried over $MgSO_4$ and concentrated to afford 1-aminomethyl-1-cyclohexanol which is mixed with DMSO (3 ml) and 1-ethyl-6-methoxy-1H-pyrazolo[3,4-b]quinoline (0.8 g, 3 mmol). The reaction mixture is stirred at 110° C. overnight, and then is partitioned between water and $CH_2Cl_2$. The $CH_2Cl_2$ layer is separated, dried, filtered and evaporated. The residue is crystallized from and recrystallized from acetonitrile to afford 0.65 g of 1-ethyl-6-methoxy-N-[(1-hydroxycyclohexyl)methyl]-1H-pyrazolo[3,4-b]quinolin-4-amine, m.p. 201°–203° C.

EXAMPLE 33

A mixture of DMSO (6 ml), chloroethylmorpholine hydrochloride (1.23 g, 6.6 mmol), 1-ethyl-6-hydroxy-N-(cyclohexylmethyl)-1H-pyrazolo[3,4-b]quinolin-4-amine (2 g, 6.6 mmol) and KOH (1 g) is stirred at room temperature overnight. The reaction mixture is partitioned between $CH_2Cl_2$ and water and the $CH_2Cl_2$ layer is separated and evaporated. The residue is purified by column chromatography on silica gel eluting with 10% ethanol/ethyl acetate to afford the product as the free base. The free base is recrystallized from hot ethyl acetate/hexane to afford 0.425 g of 1-ethyl-6-[2-(4-morpholinyl)ethoxy]-N-(cyclohexylmethyl)-1H-pyrazolo[3,4-b]quinolin-4-amine, as a yellow powder, m.p. 176°–178° C.

EXAMPLE 34

A mixture of S(+)-1-cyclohexylethylamine (2.0 ml, 13.6 mmol), 1-ethyl-6-nitro-4-chloro-1H-pyrazolo[3,4-b]quinoline (2.76 g, 0.01 mol), DMSO (10 ml) and triethylamine (3 ml, 0.01 mol) is heated at 110° C. overnight. The reaction mixture is partitioned between $CH_2Cl_2$ and water, and then the $CH_2Cl_2$ layer is separated and evaporated. The residue is crystallized from ethanol (40 ml) and collected by filtration. The solid is dissolved in warm methanol (100 ml) and then is treated with methanesulfonic acid. The methanol is evaporated to a volume of about 5 ml, and the solid which crystallizes from the solution is collected by filtration and washed with methanol and then ether to afford 1.71 g of 1-ethyl-6-nitro-N-[S(+)-1-(cyclohexyl)ethyl]-1H-pyrazolo[3,4-b]quinolin-4-amine. $CH_3SO_3H$, m.p. 176°–178° C.

EXAMPLE 35

A mixture of R-(−)-1-cyclohexylethylamine (0.59 ml, 4 mmol), DMSO (2 ml) and 1-ethyl-6-nitro-4-chloro-1H-pyrazolo[3,4-b]quinoline (0.55 g, 2 mmol) is heated at 110° C. for 6 hours. The reaction mixture is cooled and then is partitioned between water (50 ml) and $CH_2Cl_2$ (50 ml). The $CH_2Cl_2$ layer is separated, washed with water, dried over $MgSO_4$, filtered and evaporated. The residue is purified by column chromatography on silica gel eluting with 50% ether/hexane/10% $CH_2Cl_2$ to afford the product as the free base. The free base is converted into the methanesulfonic acid salt following a procedure similar to that described in Example 34 to afford 0.435 g of 1-ethyl-6-nitro-N-[R(−)-1-(cyclohexyl)ethyl]-1H-pyrazolo[3,4-b]quinolin-4amine. $CH_3SO_3H$. ½ $H_2O$, m.p. 278°–279° C.

EXAMPLE 36

(a) and (b) A mixture of 1-ethyl-6-nitro-4-chloro-1H-pyrazolo[3,4-b]quinoline (2.7 g, 17.8 mmol), triethylamine (3 ml, 0.02 mol), DMSO (15 ml) and 3-hydroxycyclohexylmethylamine (4.97 g, 18 mmol) is heated at 110° C. overnight. The reaction mixture is poured into ice water (200 ml)/$NH_4OH$ (10 ml) and the solid which forms is collected by filtration. The filtrate is then extracted with $CH_2Cl_2$ (2×100 ml). The solid is stirred and sonicated with $CH_2Cl_2$ (2×200 ml), and any solids which did not go into solution are collected by filtration. All of the above $CH_2Cl_2$ filtrates and extracts are combined, washed with water and evaporated. The residue is slurried with ethyl acetate (10–15 ml)/ether (20 ml) and a red colored solid is collected by filtration and washed with ether. The solid is purified by column chromatography (2×) on silica gel (note that the solid is preloaded onto 50–100 g of silica gel) eluting with 40% THF/cyclohexane and each of the diastereomers which is isolated is dissolved in hot THF, filtered and the solvent is evaporated. Each of the residues is slurried with ethanol (5 ml), filtered and dried to afford 0.69 g of 1-ethyl-6-nitro-N-(3-hydroxycyclohexylmethyl)-1H-pyrazolo[3,4-b]quinolin-4-amine (the RS,SR diastereomer which is labelled as Example 36(a)), m.p. 236°–238° C. and 2.23 g of 1-ethyl-6-nitro-N-(3-hydroxycyclohexylmethyl)-1H-pyrazolo[3,4-b]quinolin-4-amine (the RR,SS diastereomer which is labelled as Example 36(b)), m.p. 247°–248° C.

EXAMPLE 37

(a) A solution of 2-chloro-5-(methylthio)benzoic acid (25 g, 123 mmol) dissolved in methanol (500 ml) is cooled to 0°–5° C. and then OXONE™ (227.6 g, 370 mol) in water (500 ml) is added. The reaction mixture is stirred for 30 minutes at 0°–5° C. and then at room temperature for 4 hours. The reaction mixture is diluted with water, extracted with $CHCl_3$ (3×200 ml) and the $CHCl_3$ extracts are combined, washed with water, then brine and then are dried over MgSO$_4$, filtered and evaporated to afford 5.13 g of 2-chloro-5-(methylsulfonyl)benzoic acid, m.p. 187°–188° C.

(b) A mixture of 2-chloro-5-(methylsulfonyl)benzoic acid (5.0 g, 21.4 mmol), 5-amino-1-ethylpyrazole (2.4 g, 21.4 mmol), DMF (50 ml), Cu(OAc)$_2$ (0.5 g) and K$_2$CO$_3$ (2.76 g, 20 mmol) is heated at reflux overnight. The reaction mixture is poured into water, acidified with acetic acid and extracted with CH$_2$Cl$_2$. The CH$_2$Cl$_2$ layer is evaporated to afford N-(1-ethylpyrazol-5-yl)-5-(methylsulfonyl)anthranilic acid.

(c) A mixture of N-(1-ethylpyrazol-5-yl)-5-(methylsulfonyl) anthranilic acid of example 37(b) and POCl$_3$ (50 ml) is heated at 110° C. for 16 hours. The reaction mixture is poured into ice water, neutralized with NH$_4$OH and extracted with CH$_2$Cl$_2$. The CH$_2$Cl$_2$ layer is evaporated, and the residue is purified by column chromatography on silica gel eluting with 50% ether/H$_2$Cl$_2$ to afford 1.1 g of 1-ethyl-4-chloro-6-(methylsulfonyl)-1H-pyrazolo[3,4-b] quinoline, m.p. 158°–160° C.

(d) A mixture of 1-ethyl-4-chloro-6-(methylsulfonyl)-1H-pyrazolo[3,4-b]quinoline (1.1 g, 3.56 mmol), DMSO (3 ml) and S(+)-1-cyclohexylethylamine (1.06 ml, 7.12 mmol) is heated at 110° C. overnight. The reaction mixture is partitioned between water (25 ml) and CH$_2$Cl$_2$ (25 ml), the layers are separated, and the aqueous layer is extracted with CH$_2$Cl$_2$ (25 ml). The CH$_2$Cl$_2$ extracts are combined, washed with water, dried over MgSO$_4$, and evaporated. The residue is purified by column chromatography on silica gel eluting with 50% CH$_2$Cl$_2$/30% hexane/20% ethyl acetate to afford 1-ethyl-6-(methylsulfonyl)-N-[S(+)-1-(cyclohexyl)ethyl]-1H-pyrazolo[3,4-b]quinolin-4-amine, [alpha]$^{25}$D=+119.6° (C=1% CHCl$_3$).

EXAMPLE 38

(a) and (b) A mixture of 1-benzyl-4-chloro-1H-pyrazolo[3,4-b]quinoline (5.86 g, 0.02 mol), DMSO (20 ml) and S(+)-1-cyclohexylethylamine (5.1 g, 0.04 mol) is heated at 110°–120° C. for 18 hours. The reaction mixture is cooled to room temperature, then is poured into ice water. The resulting solid is collected by filtration, washed with water and dried to give 7.8 g of crude product which is purified by column chromatography on silca gel eluting with CH$_2$Cl$_2$/ether (9/1) to afford 6.1 g (79%) of 1-benzyl-N-[S(+)-1(cyclohexyl)ethyl]-1H-pyrazolo[3,4-b]quinolin-4-amine (labelled as Example 38(a). The free base (0.6 g) is dissolved in CH$_2$Cl$_2$ and treated with ethereal HCl, and the resulting salt is collected by filtration and dried to afford 0.5 g of 1-benzyl-N-[S(+)-1-(cyclohexyl)ethyl]-1H-pyrazolo[3,4-b] quinolin-4-amine.HCl (labeled as Example 38(b)), as a white solid, m.p. 260°–262° C.

EXAMPLE 39

A mixture of 1-ethyl-4-chloro-1H-pyrazolo[3,4-b] quinoline (1 g), DMSO (3 ml) and S(+)-1-cyclohexylethylamine (1 ml) is heated at 110° C. overnight. The reaction mixture is cooled, then is partitioned between water (25 ml) and CH$_2$Cl$_2$ (25 L). The layers are separated and the CH$_2$Cl$_2$ layer is evaporated. The residue is purified by column chromatography on silica gel eluting with 70% ethyl acetate/hexane to afford an oil which is crystallized from hexane and recrystallized from ether/hexane to afford 0.65g of 1-ethyl-N-[S(+)-1-(cyclohexyl)ethyl]-1H-pyrazolo [3,4-b]quinolin-4-amine, m.p. 135°–136°, [alpha]$^{25}$D=+66.0 (C=1% CHCl$_3$).

EXAMPLE 40

(a) A mixture of D-(-)-alpha-aminophenylacetic acid ethyl ester hydrochloride (10.8 g, 0.05 mol), ethanol (50 ml) and rhodium on alumina (0.5 g) is hydrogenated on a Parr apparatus at 50 psi and 40° C. for 5 hours. Additional catalyst (1 g) is added, and the mixture is hydrogenated at 50 psi and 40° C. for one day. The catalyst is filtered off, the filtrate is evaporated, and the residue is washed with ether to afford R-(-)-alpha-aminocyclohexyl acetic acid ethyl ester hydrochloride, as a white solid, m.p. 179°–180° C., [alpha]$^{25}$D=-20.1° (C=1% CHCl$_3$).

(b) A mixture of R-(-)-alpha-aminocyclohexylacetic acid ethyl ester hydrochloride (3.0 g, 13.6 mmol), LAH (30 g) and THF (50 ml) is stirred in an ice bath for 1 hour, then at 60° C. for 3 hours and finally at reflux for 0.5 hours. The reaction mixture is quenched with water (3 ml), 10% NaOH (3 ml) and then water (9 ml). The solids that form are collected by filtration and washed with THF and ether. The filtrate is dried over MgSO$_4$, filtered and concentrated in vacuo to afford, after recrystallization from hot hexane, 1.273 g of R-(-)-2-(cyclohexyl)-2-aminoethanol, m.p. 86°–87° C, [alpha]$^{25}$ D=-14.3° (c=1% CHCl$_3$).

(c) A mixture of 1-ethyl-4-chloro-6-nitro-1H-pyrazolo[3,4-b]quinoline (1.0 g), R-(-)-2-(cyclohexyl)-2-aminoethanol (1.0 g) and DMSO is heated at 110° C. overnight. The reaction mixture is partitioned between CH$_2$Cl$_2$ and water, and then the CH$_2$Cl$_2$ layer is separated and evaporated. The residue is purified by column chromatography on silica gel eluting with ethyl acetate/hexane/CH$_2$Cl$_2$, and the resulting product is crystallized ethanol and then recrystallized from ethanol to afford 0.66 g of 1-ethyl-6-nitro-N-[R-(-)-1-(cyclohexyl)ethanol]-1H-pyrazolo[3,4-b]quinolin-4-amine, m.p. 249°–250° C.

EXAMPLE 41

(a) A mixture of S(+)-1-cyclohexylethylamine (0.9 g, 7 mmol), DMSO (5 ml) and 1-ethyl-6-bromo-4-chloro-1H-pyrazolo[3,4-b]quinoline (1.1 g, 3.5 mmol) is heated at 110°–120° C. for 18 hours. The reaction mixture is cooled to room temperature, then is poured into ice water. The product is isolated by filtration and purified by column chromatography on silica gel eluting with CH$_2$Cl$_2$/ether (8/2) to afford 0.89 g (62%) of 1-ethyl-6-bromo-N-[S(+)-(1-cyclohexyl)ethyl]-1H-pyrazolo[3,4-b]quinolin.4-amine.

(b) and (c) A suspension of 1-ethyl-6-bromo-N-[S(+)-(1-cyclohexyl)ethyl-1H-pyrazolo[3,4-b]quinolin-4-amine (0.88 g, 2.2 mmol), DMF (10 ml) and copper (I) cyanide (0.22 g, 2.5 mmol) is refluxed for 24 hours. Additional CuCN (0.22 g) is added and the mixture is refluxed for about 2 days. The reaction mixture is filtered, and the filtrate is evaporated to dryness. The residue is dissolved in CH$_2$Cl$_2$, washed with NH$_4$OH and the CH$_2$Cl$_2$ layer is dried over MgSO$_4$, and evaporated to dryness. The residue is purified by column chromatography on silica gel eluting with CH$_2$Cl$_2$/ether (9/1) to afford 0.48 g (63%) of 1-ethyl-6-bromo-N-[S(+)-(1-cyclohexyl)ethyl]-1H-pyrazolo[3,4-b] quinolin-4-amine (labeled as Example 41(b)). The free base is dissolved in ether/CH$_2$Cl$_2$, and the ethereal HCl is added. The resulting solid is collected by filtration and recrystallized from isopropanol/ether to afford 0.35 g of 1-ethyl-6-cyano-N-[S(+)-(1-cyclohexyl)ethyl]-1H-pyrazolo[3,4-b] quinolin-4-amine.HCl (labeled Example 41(c)), as a yellow solid, m.p. 298°–300° C.

EXAMPLE 42

(a) A mixture of 5-amino-1-ethylpyrazole (5.0 g, 45 mmol), 2-bromo-4,5-dimethoxybenzoic acid (11.76 g, 45 mmol), K$_2$CO$_3$ (6.21 g, 45 mmol), Cu(OAc)2 (0.8 g, 400 mmol) and DMF (125 ml) is refluxed overnight. The reaction mixture is cooled, poured into water and acidified with acetic acid. The resulting solid is collected by filtration and dried to afford 12.8 g (97%) of N-(1-ethylpyrazol-5-yl)-4,5-dimethoxyanthranilic acid.

(b) A mixture of N-(1-ethylpyrazol-5-yl)-4,5-dimethoxy anthranilic acid (12.8 g, 44 mmol) and $POCl_3$ (75 ml) is refluxed for 8 hours. The reaction mixture is cooled to room temperature, poured into ice water and neutralized with concentrated $NH_4OH$. The mixture is extracted with $CH_2Cl_2$, and the $CH_2Cl_2$ layer is dried over $MgSO_4$ and evaporated to dryness. The residue is purified by column chromatography on silica gel eluting with $CH_2Cl_2$/ether (9/1) to afford 8.0 g (62%) of 1-ethyl-4-chloro-6,7-dimethoxy-1H-pyrazolo[3,4-b]quinoline.

(c) A mixture of 1-ethyl-4-chloro-6,7-dimethoxy-1H-pyrazolo[-3,4-b]quinoline (8.0 g, 27.44 mmol), DMSO (20 ml) and S(+)-1-cyclohexylethylamine (8 ml, 54.88 mmol) is heated at 100°–110° C. overnight, then at 130°–140° C. for 48 hours. The reaction mixture is cooled to room temperature and then is poured into ice water. The resulting product is collected by filtration and purified by column chromatography on silica gel eluting with $CH_2C_2$/ether (4/1) to afford 9.3 g of the product as the free base. The free base (1.0 g) is dissolved in $CH_2Cl_2$ and treated with ethereal HCl to afford a gummy salt which crystallized on standing. The hydrochloride salt is recrystallized from isopropanol/ether to afford 0.7 g of 1-ethyl-6,7-dimethoxy-N-[S(+)-1-(cyclohexyl)ethyl-1H-pyrazolo[3,4-b]quinolin-4-amine.HCl. ¼ hydrate, m.p. 185°–187° C. (dec.), $[alpha]^{25}D=+123°$ (C=1% methanol).

EXAMPLE 43

A mixture of 1-ethyl-6-bromo-N-[S(+)-1-(cyclohexyl)ethyl]-1H-pyrazolo[3,4-b]quinolin-4-amine (10 g, 2.5 mmol) and imidazole (0.51 g, 7.5 mmol) is heated at 120°–130° C. for 6 hours, then at 170°–180° C. overnight. N-Methyl-2-pyrrolidinone (2 ml) is added and the mixture is heated at 170°–180° C. for 2 hours. Starting material is still present, so $K_2CO_3$ (0.5 g, 3.6 mmol) and a catalytic amount of $Cu(OAc)_2$ are added, and the mixture is heated at 160°–170° C. for about 2 days. The reaction mixture is cooled to room temperature and then is poured into ice water. The resulting solid is collected by filtration, washed with water and dried. The solid residue is dissolved in methanol and treated with an equivalent amount of methanesulfonic acid. A gummy solid form which is dissolved in $CH_2Cl_2$ and neutralized with concentrated NHOH. The $CH_2Cl_2$ layer is separated, dried over $MgSO_4$ and evaporated to dryness. The solid residue is recrystallized from $CH_2Cl_2$/ethyl acetate to afford 0.51 g (52%) of 1-ethyl- 6-(1-imidazolyl)-N-[S(+)-1-(cyclohexyl)ethyl]-1H-pyrazolo[3,4-b]quinolin-4-amine, as a yellow solid, m.p. 256°–258° C.

EXAMPLE 44

(a) A mixture of 5-amino-1-ethylpyrazole (33.7 g, 0.3 mol), 2,5-dibromobenzoic acid (84 g, 0.3 mol), $K_2CO_3$ (41.4 g, 0.3 mol), $Cu(OAc)2$ (1 g) and DMF (500 ml) is refluxed overnight. The reaction mixture is poured into ice water (4 L), and is then acidified with acetic acid. The solid which forms is collected by filtration and dried to afford 35 g of a mixture of N-(1-ethylpyrazol-5-yl)-3-bromoanthranilic acid and N-(1-ethylpyrazol-5-yl)-5-bromoanthranilic acid.

(b) and (c) A mixture of N-(1-ethylpyrazol-5-yl)-3-bromoanthranilic acid and N-(1-ethylpyrazol-5-yl)-5-bromoanthranilic acid (34.8 g, 0.11 mol) and $POCl_3$ (100 ml) is heated at reflux for 8 hours. The reaction mixture is cooled to room temperature, and then is poured into ice water and neutralized with concentrated $NH_4OH$. The mixture is extracted with $CH_2Cl_2$ and the $CH_2Cl_2$ layer is dried over $MgSO_4$ and evaporated to dryness. The residue is purified by column chromatography on silica gel eluting with $CH_2Cl_2$/ether (9/1) to afford 2.7 g of 1-ethyl-4-chloro-8-bromo-1H-pyrazolo[3,4-b]quinoline (labelled as Example 44(b)) and 22.5 g (64%) of 1-ethyl-4-chloro-6-bromo-1H-pyrazolo[3,4-b]quinoline (labelled as Example 44(c)).

(d) A mixture of 1-ethyl-4-chloro-8-bromo-1H-pyrazolo [3,4-b]quinoline (2.0 g, 6.44 mmol), DMSO (5 ml) and cyclohexylmethylamine (1.46 g, 12.9 mmol) is heated at 80°–90° C. for 3 hours. The reaction mixture is cooled to room temperature and then is poured into water. The resulting solid is collected by filtration, washed with water and evaporated. The residue is purified by column chromatography on silica gel eluting with $CH_2Cl_2$/ether (9/1) to afford 2.0 g (80%) of 1-ethyl-8-bromo-N-(cyclohexylmethyl)-1H-pyrazolo[3,4-b]quinolin-4-amine, as a yellow solid, m.p. 160°–162° C.

EXAMPLE 45

(a) A mixture of 2-chloro-5-(fluorosulfonyl)benzoic acid (11.93 g, 0.05 mol), diethylamine (10.97 g, 0.15 mol) and 1,2-dichloroethane (100 ml) is refluxed for 8 hours. The reaction mixture is evaporated, and the residue is dissolved in ethyl acetate. A solid is collected by filtration, and the filtrate is evaporated to dryness to afford 15.5 g of 2-chloro-5-diethylaminosulfonyl)benzoic acid.

(b) A mixture of 5-amino-1-isopropylpyrazole (6.43 g, 0.051 mol), 2-chloro-5-(diethylaminosulfonyl)benzoic acid (15.0 g, 0.051 mol), $K_2CO_3$ (7.04 g, 0.051 mol), $Cu(OAc)2$ (1.0 g) and DMF (100 ml) is refluxed for 24 hours. The reaction mixture is concentrated in vacuo, and the residue is poured into water and neutralized with acetic acid. The mixture is extracted with $CH_2Cl_2$ and the $CH_2Cl_2$ layer is dried over $MgSO_4$ and evaporated to afford 12.1 g of N-(1-isopropylpyrazol-5-yl)-5-(diethylaminosulfonyl) anthranilic acid.

(c) A mixture of N-(1-isopropylpyrazol-5-yl)-5-(diethylaminosulfonyl) anthranilic acid (12.0 g, 0.031 mol) and $POCl_3$ (80 ml) is refluxed for 6 hours. The reaction mixture is cooled to room temperature, and then is poured into ice water and neutralized with concentrated $NH_4OH$. The mixture is extracted with $CH_2Cl_2$ and the $CH_2Cl_2$ layer is dried over $MgSO_4$ and evaporated to dryness. The residue is purified by column chromatography on silica gel eluting with $CH_2Cl_2$/ether (9/1) to afford 10 g of crude 1-isopropyl-6-(diethylaminosulfonyl)-4-chloro-1H-pyrazolo[3,4-b] quinoline.

(d) A mixture of 1-isopropyl-6-(diethylaminosulfonyl)-4-chloro-1H-pyrazolo[3,4-b]quinoline (1.0 g, 2.63 mmol), DMSO (2.5 ml) and cyclohexylmethylamine (0.6 g, 5.3 mmol) is heated at 120°–130° C. for 18 hours. The reaction mixture is cooled to room temperature and then is poured into ice water. The mixture is extracted with $CH_2Cl_2$ and the $CH_2Cl_2$ layer is dried over $MgSO_4$ and evaporated to dryness. The residue is purified by column chromatography on silica gel eluting with $CH_2Cl_2$/ether (9/1) to afford 0.13 g of the product as the free base. The free base is dissolved in $CH_2Cl_2$ and is treated with ethereal.HCl. The solvent is decanted, and the residue is treated with ether to afford, after recrystallization from $CH_2Cl_2$/ether, 0.11 g of 1-isopropyl-6-(diethylaminosulfonyl)-N-(cyclohexylmethyl)-1H-pyrazolo[3,4-b]quinolin-4-amine.HCl, as an off-white solid, m.p. 170°–172° C. (dec.).

EXAMPLE 46

A mixture of 1-ethyl-4-chloro-6-bromo-1H-pyrazolo[3,4-b]quinolin-4-amine (15.53 g, 0.05 mol), S(+)-1-cyclohexylethylamine (12.73 g, 0.1 mol) and DMSO (20 ml) is heated at 120°–130° C. for 20 hours. The reaction mixture is cooled to room temperature and then is poured into ice water. The resulting solid is collected by filtration, washed with water and dried to afford 19.6 g of crude product. The crude product (1.5 g) is purified by column chromatography on silica gel eluting with $CH_2Cl_2$/ether (9/1), followed by recrystallization from ether/hexane to afford 1.0 g of 1-ethyl-6-bromo-N-[S(+)-1-(cyclohexyl) ethyl]-1H-pyrazolo[3,4-b]quinolin-4-amine, m.p. 148°–150° C., $[alpha]^{25}$ D=+83.3° (C=1% methanol).

EXAMPLE 47

(a) A mixture of 1-ethyl-6-bromo-N-[S(+)-1-(cyclohexyl)ethyl]-1H-pyrazolo[3,4-b]quinolin-4-amine (5.0 g, 12.47 mmol), CuCN (3.35 g, 37.41 mmol), NaCN (1.83 g, 37.41. mmol) and DMF (35 ml) is refluxed for about 3 days. The reaction mixture is evaporated to dryness, and the residue is partitioned between $CH_2Cl_2$ and concentrated $NH_4OH$. The $CH_2Cl_2$ layer is separated, washed with water, dried over $MgSO_4$ and concentrated in vacuo to afford 4.5 g of 1-ethyl-6-cyano-N-[S(+)-1-(cyclohexyl)ethyl]-1H-pyrazolo[3,4-b]quinolin-4-amine.

(b) To a solution of sodium methoxide (prepared from methanol (80 ml) and sodium metal (0.6 g, 26 mmol)) is added hydroxylamine hydrochloride, and the mixture is stirred at room temperature for 1.5 hours. The reaction mixture is filtered, and the filtrate is added to 1-ethyl-6-cyano-N-[S(+)-1-(cyclohexyl)ethyl]-1H-pyrazolo[3,4-b]quinolin-4-amine (4.5 g, 13 mmol). The resulting mixture is refluxed for 48 hours, and then the solvent is evaporated to dryness to afford 4.7 g of 1-ethyl-6-[C(=NOH)$NH_2$]-N-[S(+)-1(cyclohexyl)ethyl]-1H-pyrazolo[3,4-b]quinolin-4-amine.

(c) A mixture of 1-ethyl-6-[C(=NOH)$NH_2$]-N-[S(+)-1-(cyclohexyl)ethyl]-1H-pyrazolo[3,4-b]quinolin-4-amine (4.7 g, 12.37 mmol) and acetic anhydride (20 ml) is heated at 120° C. for 2 hours. The solvent is removed in vacuo, and water is added to the residue. The mixture is neutralized with saturated $K_2CO_3$, and then is extracted with ethyl acetate. The organic layer is dried over $MgSO_4$ and evaporated. The residue is purified by column chromatography on silica gel eluting with $CH_2Cl_2$/ether (9/1) to afford, after recrystallization from ether/hexane, 0.6 g of 1-ethyl-6-[5-methyl-3-(1,2,4-oxadiazolyl)-N-[S(+)-1-(cyclohexyl)ethyl]-1H-pyrazolo[3,4-b]quinolin-4-amine. ¼ $H_2O$, as a yellow solid, m.p. 113°–115° C.

EXAMPLE 48

(a) A mixture of 2-chloro-5-(methylthio)benzoic acid (8.8 g, 0.043 mol), DMF (100 ml), 5-amino-1-ethylpyrazole (4.8 g, 0.043 mol), $K_2CO_3$ (5.94 g, 0.043 mol) and Cu(OAc)2 (0.5 g) is refluxed overnight. The reaction mixture is cooled to room temperature, poured into water and acidified with acetic acid to a pH of about 4–5. The mixture is extracted with $CH_2Cl_2$ and then the $CH_2Cl_2$ layer is evaporated to afford 4.5 g of N-(1-ethylpyrazol-5-yl)-5-(methylthio) anthranilic acid.

(b) A mixture of N-(1-ethylpyrazol-5-yl)-5-(methylthio) anthranilic acid (4.5 g) and $POCl_3$ (20 ml) is refluxed overnight. The reaction mixture is poured into water, then ice is added. The mixture is extracted with $CH_2Cl_2$ and then the $CH_2Cl_2$ layer is evaporated. The residue is purified by column chromatography on silica gel eluting with 50% ethyl acetate/hexane to afford 2.4 g of 1-ethyl-4-chloro-6-(methylthio)-1H-pyrazolo[3,4-b]quinoline, m.p. 120°–121° C.

(c) To a solution of 1-ethyl-4-chloro-6-(methylthio)-1H-pyrazolo[3,4-b]quinoline (2.4 g, 8.7 mmol) in $CHCl_3$ (50 ml) at –40° C. is added m-chloroperoxybenzoic acid (2.75 g, 8.7 mmol). The reaction mixture is slowly warmed to 0° C. and then saturated $NaHCO_3$ (10 ml) is added. The reaction mixture is partitioned between water (20 ml) and $CH_2Cl_2$ (20 ml), the layers are separated and then the aqueous layer is extracted with $CH_2Cl_2$ (20 ml). The $CH_2Cl_2$ extracts are combined, dried over $MgSO_4$ and evaporated. The residue is purified by column chromatography on silica gel eluting with 50% ether/hexane, then 25% ethyl acetate/25% hexane/ 50% ether and finally ethyl acetate (100%) to afford 2.4 g of 1-ethyl-4-chloro-6-(methylsulfinyl)-1H-pyrazolo[3,4-b]quinoline.

(d) and (e) A mixture 1-ethyl-4-chloro-6-(methylsulfinyl)-1H-pyrazolo[3,4-b]quinoline (2.0 g, 0.014 mol), DMSO (5 ml) and S(+)-1cyclohexylethylamine (4.2 ml, 0.028 mol) is heated at 110° C. overnight. The reaction mixture is cooled, then is partitioned between $CH_2Cl_2$ (30 ml) and water (30 ml) containing $NH_4OH$ (5 ml). The layers are separated, and the aqueous layer is extracted with $CH_2Cl_2$. The $CH_2Cl_2$ extracts are combined and evaporated to dryness, and the residue is passed through a silica gel column eluting with ethyl acetate to afford the product as a mixture of diastereomers. The diasteromers are separated by repeated recrystallizations from hot ethyl acetate to afford 1-ethyl-6-(methylsulfinyl)-N-[S(+)-1-(cyclohexyl)ethyl]-1H-pyrazolo [3,4-b]quinolin-4-amine [one diasteromer of which is labelled as Example 48(d), m p 195°–196° C. [alpha] <23.8>D=+47.9° (C=20 mg/2 ml of $CDCl_3$ ), and the other diasteromer of which is labelled as Example 48(e), m.p. 235°–236° C. $[+]^{23.8}$ D=+217.6° (C=20 mg/2 ml of $CDCl_3$)].

EXAMPLE 49

A mixture of 1-ethyl-4-chloro-6-(methylsulfinyl)-1H-pyrazolo[3,4-b]quinoline (0.4 g, 2.8 mmol), DMSO (1.5 ml) and cyclohexylmethylamine (0.73 ml, 5.6 mmol) is heated at 110° C. over night. The reaction mixture is cooled to room temperature, then is partitioned between $CHCl_3$ (20 ml) and water (20 ml) containing $NH_4OH$ (3 ml). The layers are separated, the aqueous layer is extracted with $CH_2Cl_2$ (10 ml), and the organic layers are combined dried over $MgSO_4$ and evaporated. The residue is purified by column chromatography on silica gel eluting with ethyl acetate, followed by recrystallization from ethyl acetate (2×) to afford 0.115 g of 1-ethyl-6-(methylsulfinyl)-N-(cyclohexylmethyl)-1H-pyrazolo[3,4-b]quinolin-4-amine, m.p. 186°–187° C.

EXAMPLE 50

A mixture of 1-ethyl-6-bromo-N-[S(+)-1-(cyclohexyl) ethyl]-1H-pyrazolo[3,4-b]quinolin-4-amine (1.0 g, 2.5 mmol), 4-methylpyrazole (1.0 g, 12.18 mmol), $K_2CO_3$ (1.0 g, 7.2 mmol), Cu(OAc)2 (catalytic amount) and N-methyl-2-pyrrolidinone (3 ml) is heated at about 160°–170° C. for about 2 days. The reaction mixture is cooled to room temperature, CH2Cl2 is added and then the mixture is poured into ice water. The $CH_2Cl_2$ layer is separated, dried over $MgSO_4$ and evaporated to dryness. The residue is purified by column chromatography on silica gel eluting with $CH_2Cl_2$/ether (9/1) to afford 1.0 g of the product as the free base. The free base is dissolved in ether, treated with ethereal.HCl and then is triturated with ether. The resulting salt is collected by filtration, washed with ether and dried to afford, after recrystallization from $CH_2Cl_2$/ether (2×), 0.48 g of 1-ethyl-6-(4-methyl-1-pyrazolyl)-N-[S(+)-1-(cyclohexyl)ethyl]-1H-pyrazolo[3,4-b]quinolin-4-amine.HCl, m.p. 310°–312° C.

EXAMPLE 51

A mixture of 1-ethyl-6,7-dimethoxy-N-[S(+)-1-(cyclohexyl)ethyl]-1H-pyrazolo[3,4-b]quinolin-4-amine (1.0 g, 2.6 mmol) and pyridine hydrochloride (1.0 g, 8.65 mmol) is heated for four hours and then is cooled to room temperature. Water is added to the reaction mixture and the resulting solid is collected by filtration, washed with water and dissolved in 5N NaOH. The aqueous layer is neutralized with acetic acid, and the resulting solid is collected by filtration, washed with water and dried to afford 0.66 g of crude product. The crude product is recrystallized from ethanol to afford 0.55 g of 1-ethyl-6,7-dimethoxy-N-[S(+)-1-(cyclohexyl)ethyl]-1H-pyrazolo[3,4-b]quinolin-4-amine. ¾ $H_2O$, m.p. >250° C.

EXAMPLE 52

A mixture 1-ethyl-6-bromo-N-[S(+)-1-(cyclohexyl)ethyl]-1H-pyrazolo[3,4-b]quinolin-4-amine (1.0 g, 2.5 mmol), pyrazole (0.83 g, 12.18 mmol), $K_2CO_3$ (1.0 g, 7.2 mmol), Cu(OAc)2 (catalytic amount) and N-methyl-2-pyrrolidinone (3 ml) is heated at about 160°–170° C. for about 4 days. The reaction mixture is cooled to room temperature and then is poured into an excess of ice water. The resulting solid is collected by filtration, washed with water and dried to afford 1.3 g of crude product. The crude product is purified by column chromatography on silica gel eluting with $CH_2Cl_2$/ether (9/1) to afford 0.56 g (58%) of the product as the free base. The free base is dissolved in ether and treated with ethereal.HCl. The resulting salt is collected by filtration, washed with ether, dried and then is recrystallized from acetonitrile to afford 0.47 g of 1-ethyl- 6-(1-pyrazolyl)-N-[S(+)-1-(cyclohexyl)ethyl]-1H-pyrazolo[3,4-b]quinolin-4-amine.HCl, m.p. 278°–280° C., [alpha]$^{25}$ D=+150° (C=1% methanol).

EXAMPLE 53

(a) A mixture of 5-amino-1-ethylpyrazole (0.56 g, 5 mmol), 2-chloro-5-(trifluoromethylsulfonyl)benzoic acid (1.4 g, 4.9 mmol), $K_2CO_3$ (0.69 g, 5 mmol), Cu(OAc)<2> (0.1 g) and DMF (10 ml) is refluxed for 4 hours and then is cooled to room temperature and is allowed to stand for about 3 days. Water is added to the reaction mixture, and then the solution is acidified with acetic acid to a pH of about 5. The mixture is extracted with $CH_2Cl_2$ and then the $CH_2Cl_2$ layer is evaporated to afford N-(1-ethylpyrazol-5-yl)-5-trifluoromethylsulfonyl)anthranilic acid.

(b) A mixture of N-(1-ethylpyrazol-5-yl)-5-(trifluoromethylsulfonyl)anthranilic acid and $POCl_3$ (30 ml) is heated on a steam bath overnight. The reaction mixture is poured onto ice waterl and then is neutralized with $NH_4OH$. The resulting solid is collected by filtration, washed with water, dissolved in $CH_2Cl_2$, dried over $MgSO_4$, filtered and stripped. The residue is purified by column chromatography on silica gel eluting with 10% ethyl acetate/hexane to afford 1.0 g of 1-ethyl-4-chloro-6-(trifluoromethylsulfonyl)-1H-pyrazolo[3,4-b]quinoline.

(c) A mixture of 1-ethyl-4-chloro-6-(trifluoromethylsulfonyl)-1H-pyrazolo[3,4-b]quinoline (1.0 g, 3.1 mmol), DMSO and S(+)-1-cyclohexylethylamine (0.79 g, 6.2 mmol) is heated at 110° C. overnight. The reaction mixture is cooled to room temperature and then is partitioned between $CH_2Cl_2$ (50 ml) and aqueous $NH_4OH$. The $CH_2Cl_2$ layer is washed with water, then brine and then the solvent is evaporated. The residue is purified by column chromatography on silica gel eluting with 50% ethyl acetate/hexane to afford an oil which is treated with ethereal HCl to afford 285 mg of 1-ethyl-6-(trifluoromethylsulfonyl)-N-[S(+)-1-(cyclohexyl)ethyl]-1H-pyrazolo[3,4-b]quinolin-4-amine.HCl, m.p. 175°–185° C., [alpha]$^{25}$ D=+101° (C=1% $CHCl_3$).

EXAMPLE 54

A mixture of 1-ethyl-4-chloro-6-nitro-1H-pyrazolo[3,4-b]quinoline (0.84 g, 3 mmol), DMSO (2 ml), triethylamine (0.42 ml), 3 mmol) and S(+)-1-cyclohexylpropylamine (0.43 g, 3 mmol) is heated at 110° C. for 5 hours. The reaction mixture is cooled to room temperature, and then is partitioned between water (40 ml) containing $NH_4OH$ (5 ml) and $CH_2Cl_2$ (50 ml). The layers are separated and the aqueous layer is extracted with $CH_2Cl_2$ (2×50 ml). The $CH_2Cl_2$ extracts are combined, washed with water (20 ml) and then evaporated. The residue is purified by column chromatography on silica gel eluting with ethyl acetate to afford the product as the free base. The free base is dissolved in ether, treated with ethereal HCl, and the solution is evaporated. The residue is crystallized from $CH_2Cl_2$/ether to afford 745 mg of 1-ethyl-6-nitro-N-[S(+)-1-(cyclohexyl)propyl]-1H-pyrazolo[3,4-b]quinolin-4-amine.HCl.

EXAMPLE 55

A mixture of 1-ethyl-6-bromo-N-[S(+)-1-(cyclohexyl)ethyl]-1H-pyrazolo[3,4-b]quinolin-4-amine (4.01 g, 10 mmol), DMF (10 ml), $CH_2$=CHSn(n-butyl)3 (3.5 g, 11 mmol) and $(Ph_3P)_2PdCl_2$ (100 mg, 0.14 mmol) is refluxed for 4 days. The reaction mixture is evaporated to dryness and then the residue is dissolved in $CH_2Cl_2$ and washed with water and then a 10% NaF solution. The $CH_2Cl_2$ layer is dried over $MgSO_4$, the solvent is removed and the residue is purified by column chromatography on silica gel eluting with 20% ethyl acetate/hexane to afford, after recrystallization from ether/hexane, 0.21 g of 1-ethyl-6-(ethenyl)-N-[S(+)-1(cyclohexyl) ethyl]-1H-pyrazolo[3,4-b]quinolin-4-amine. ¼ $H_2O$, m.p. 133°–135° C.

The compounds useful in this invention can be formulated with pharmaceutically acceptable carriers into unit dosage forms in a conventional manner so that the patient in need of therapy for precancerous lesions can periodically (e.g., once or more per day) take a compound according to the method of this invention. The exact initial dose of the compounds of this invention can be determined with reasonable experimentation. One skilled in the art should understand that the initial dosage should be sufficient to achieve a blood plasma concentration approaching a percentage of the $IC_{50}$ value of the compound, with the percentage depending on the chemopreventative or chemotherapeutic indication. The initial dosage calculation would also take into consideration several factors, such as the formulation and mode of administration, e.g. oral or intravenous, of the particular compound. A patient with an average circulatory system volume of about four liters should receive an average daily dose of 1.3 μ—28 mg, preferably 0.6 mg.

It will be understood that various changes and modifications can be made in the details of procedure, formulation and use without departing from the spirit of the invention, especially as defined in the following claims.

We claim:

1. A method of treating a mammal having precancerous lesions comprising administering a pharmacologically effective amount of a compound of Formula I or pharmaceutically acceptable salt thereof:

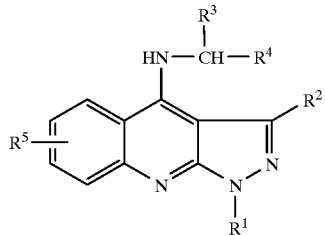

wherein $R_1$ is selected from the group consisting of lower-alkyl, phenyl-lower-alkyl, or cycloalkyl; $R_2$ is selected from the group consisting of hydrogen or lower-alkyl; $R_3$ is selected from the group consisting of hydrogen, lower-alkyl or hydroxylower-alkyl;

$R_4$ is selected from the group consisting of cycloalkyl or cylcoalkyl substituted by from one to two, the same or different, substituents selected from the group consisting of lower-alkoxycarbonyl, carboxy, lower-alkylthio-lower-alkoxycarbonyl, hydroxylower-alkyl, hydroxy, oxo, lower-alkoxy, lower-alkyl, and halogen; and $R_5$ is from one to three, the same or different, substituents selected from the group consisting of hydrogen, lower-alkoxy, hydroxy, dilower-alkylamino-lower-alkoxy, carboxylower-alkoxy, lower-alkoxycarbonyl-lower-alkoxy, nitro, polyhydroxylower-alkoxy, amino, epoxylower-alkoxy, carboxy, lower-alkanoylamino, lower-alkoxycarbonyl, pyridinyl, 4-morpholinyl-lower-alkoxy, lower-alkylsulfonyl, cyano, 1-imidazolyl, halogen, dilower-alkylaminosulfonyl, oxadiazolyl, or oxadiazolyl substituted on any available carbon atom thereof by lower-alkyl, lower-alkylsulfinyl, 1-pyrazolyl, or 1-pyrazolyl substituted on any available carbon atom thereof by lower-alkyl, trifluoromethylsulfonyl, lower-alkenyl, lower-alkyl, and lower-alkynyl; or a pharmaceutically acceptable acid-addition salt and/or hydrate and/or solvate thereof, or, where applicable, a stereoisomer or a racemic mixture thereof.

2. The method of claim 1 wherein $R_4$ is cycloalkyl or cylcoalkyl substituted by one substituent selected from the group consisting of lower-alkoxycarbonyl, lower-alkylthio-lower-alkoxycarbonyl, hydroxylower-alkyl, hydroxy, and oxo; and $R_5$ is from one to two, the same or different, substituents selected from the group consisting of hydrogen, lower-alkoxy, hydroxy, dilower-alkylamino-lower-alkoxy, carboxylower-alkoxy, nitro, polyhydroxylower-alkoxy, amino, epoxylower-alkoxy, carboxy, lower-alkanoylamino, lower-alkoxycarbonyl, pyridinyl, 4-morpholinyl-lower-alkoxy, lower-alkylsulfonyl, cyano, 1-imidazolyl, halogen, dilower-alkylaminosulfonyl, oxadiazolyl substituted on any available carbon atom thereof by lower-alkyl, lower-alkylsulfinyl, 1-pyrazolyl, or 1-pyrazolyl substituted on any available carbon atom thereof by lower-alkyl, trifluoromethylsulfonyl, and lower-alkenyl.

3. The method of claim 2 wherein $R_1$ is selected from the group consisting of ethyl, isopropyl, benzyl or cyclopentyl; $R_2$ is selected from the group consisting of hydrogen or methyl; and $R_3$ is selected from the group consisting of hydrogen, methyl, ethyl or hydroxymethyl.

4. The method of claim 3 wherein $R_4$ is cycloalkyl selected from the group consisting of cyclohexyl, cyclopropyl, and adamantyl or said cycloalkyl group substituted by one substituent selected from the group consisting of methoxycarbonyl, methylthiomethoxycarbonyl, hydroxymethyl, hydroxy, and oxo; and $R_5$ is from one to two, the same or different, substituents selected from the group consisting of hydrogen, methoxy, hydroxy, 2-(dimethylamino) ethoxy, carboxymethoxy, nitro, 2,3-dihydroxypropoxy, amino, 2,3-epoxypropoxy, 1-carboxyethoxy, carboxy, acetylamino, methoxycarbonyl, pyridinyl, 2-(4-morpholinyl) ethoxy, methylsulfonyl, cyano, 1-imidazolyl, bromo, diethylaminosulfonyl, 5-methyl-3-(1,2,4-oxadiazolyl), methylsulfinyl, 4-methyl-1-pyrazolyl, 1-pyrazolyl, trifluoromethylsulfonyl, and ethenyl.

5. The method of claim 1 wherein the compound is 1-ethyl-6-nitro-N-[S(+)-1-(cyclohexyl)ethyl]-1H-pyrazolo[3,4-b]quinolin-4-amine.

6. A method for inhibiting the growth of neoplastic cells comprising exposing the cells to a growth inhibiting effective amount of a compound of Formula I or pharmaceutically acceptable salt thereof:

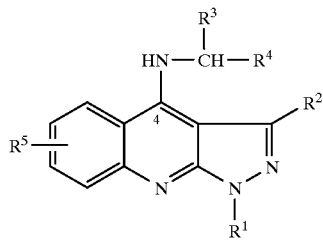

wherein: $R_1$ is selected from the group consisting of lower-alkyl, phenyl-lower-alkyl, or cycloalkyl; $R_2$ is selected from the group consisting of hydrogen or lower-alkyl; $R_3$ is selected from the group consisting of hydrogen, lower-alkyl or hydroxylower-alkyrl;

$R_4$ is selected from the group consisting of cycloalkyl or cylcoalkyl substituted by from one to two, the same or different, substituents selected from the group consisting of lower-alkoxycarbonyl, carboxy, lower-alkylthio-lower-alkoxycarbonyl, hydroxylower-alkyl, hydroxy, oxo, lower-alkoxy, lower-alkyl, and halogen; and $R_5$ is from one to three, the same or different, substituents selected from the group consisting of hydrogen, lower-alkoxy, hydroxy, dilower-alkylamino-lower-alkoxy, carboxylower-alkoxy, lower-alkoxycarbonyl-lower-alkoxy, nitro, polyhydroxylower-alkoxy, amino, epoxylower-alkoxy, carboxy, lower-alkanoylamino, lower-alkoxycarbonyl, pyridinyl, 4-morpholinyl-lower-alkoxy, lower-alkylsulfonyl, cyano, 1-imidazolyl, halogen, dilower-alkylaminosulfonyl, oxadiazolyl, or oxadiazolyl substituted on any available carbon atom thereof by lower-alkyl, lower-alkylsulfinyl, 1-pyrazolyl, or 1-pyrazolyl substituted on any available carbon atom thereof by lower-alkyl, trifluoromethylsulfonyl, lower-alkenyl, lower-alkyl, and lower-alkynyl; or a pharmaceutically acceptable acid-addition salt and/or hydrate and/or solvate thereof, or, where applicable, a stereoisomer or a racemic mixture thereof.

7. The method of claim 6 wherein $R_4$ is cycloalkyl or cylcoalkyl substituted by one substituent selected from the group consisting of lower-alkoxycarbonyl, lower-alkylthio-lower-alkoxycarbonyl, hydroxylower-alkyl, hydroxy, and oxo; and $R_5$ is from one to two, the same or different, substituents selected from the group consisting of hydrogen, lower-alkoxy, hydroxy, dilower-alkylamino-lower-alkoxy, carboxylower-alkoxy, nitro, polyhydroxylower-alkoxy, amino, epoxylower-alkoxy, carboxy, lower-alkanoylamino, lower-alkoxycarbonyl, pyridinyl, 4-morpholinyl-lower-alkoxy, lower-alkylsulfonyl, cyano, 1-imidazolyl, halogen, dilower-alkylaminosulfonyl, oxadiazolyl substituted on any available carbon atom thereof by lower-alkyl, lower-alkylsulfinyl, 1-pyrazolyl, or 1-pyrazolyl substituted on any available carbon atom thereof by lower-alkyl, trifluoromethylsulfonyl, and lower-alkenyl.

8. The method of claim 7 wherein wherein $R_1$ is selected from the group consisting of ethyl, isopropyl, benzyl or cyclopentyl; $R_2$ is selected from the group consisting of hydrogen or methyl; and $R_3$ is selected from the group consisting of hydrogen, methyl, ethyl or hydroxymethyl.

9. The method of claim 8 wherein $R_4$ is cycloalkyl selected from the group consisting of cyclohexyl, cyclopropyl, and adamantyl or said cycloalkyl group substituted by one substituent selected from the group consisting of methoxycarbonyl, methylthiomethoxycarbonyl, hydroxymethyl, hydroxy, and oxo; and $R_5$ is from one to two, the same or different, substituents selected from the group consisting of hydrogen, methoxy, hydroxy, 2-(dimethylamino) ethoxy, carboxymethoxy, nitro, 2,3-dihydroxypropoxy, amino, 2,3-epoxypropoxy, 1-carboxyethoxy, carboxy, acetylamino, methoxycarbonyl, pyridinyl, 2-(4-morpholinyl) ethoxy, methylsulfonyl, cyano, 1-imidazolyl, bromo, diethylaminosulfonyl, 5-methyl-3-(1, 2,4-oxadiazolyl), methylsulfinyl, 4-methyl-1-pyrazolyl, 1-pyrazolyl, trifluoromethylsulfonyl, and ethenyl.

10. The method of claim 6 wherein the compound is 1-ethyl-6-nitro-N-[S(+)-1-(cyclohexyl)ethyl]-1H-pyrazolo [3,4-b]quinolin-4-amine.

11. A method for regulating apoptosis in human cells comprising exposing said cells to an effective amount of a compound of the Formula:

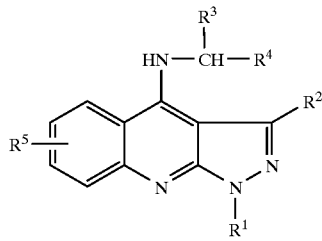

wherein: $R_1$ is selected from the group consisting of lower-alkyl, phenyl-lower-alkyl, or cycloalkyl; $R_2$ is selected from the group consisting of hydrogen or lower-alkyl; $R_3$ is selected from the group consisting of hydrogen, lower-alkyl or hydroxylower-alkyl;

$R_4$ is selected from the group consisting of cycloalkyl or cylcoalkyl substituted by from one to two, the same or different, substituents selected from the group consisting of lower-alkoxycarbonyl, carboxy, lower-alkylthio-lower-alkoxycarbonyl, hydroxylower-alkyl, hydroxy, oxo, lower-alkoxy, lower-alkyl, and halogen; and $R_5$ is from one to three, the same or different, substituents selected from the group consisting of hydrogen, lower-alkoxy, hydroxy, dilower-alklamino-lower-alkoxy, carboxylower-alkoxy, lower-alkoxycarbonyl-lower-alkoxy, nitro, polyhydroxylower-alkoxy, amino, epoxylower-alkoxy, carboxy, lower-alkanoylamino, lower-alkoxycarbonyl, pyridinyl, 4-morpholinyl-lower-alkoxy, lower-alkylsulfonyl, cyano, 1-imidazolyl, halogen, dilower-alkylaminosulfonyl, oxadiazolyl, or oxadiazolyl substituted on any available carbon atom thereof by lower-alkyl, lower-alkylsulfinyl, 1-pyrazolyl, or 1-pyrazolyl substituted on any available carbon atom thereof by lower-alkyl, trifluoromethylsulfonyl, lower-alkenyl, lower-alkyl, and lower-alkynyl; or a pharmaceutically acceptable acid-addition salt and/or hydrate and/or solvate thereof, or, where applicable, a stereoisomer or a racemic mixture thereof.

12. The method of claim 11 wherein $R_4$ is cycloalkyl or cylcoalkyl substituted by one substituent selected from the group consisting of lower-alkoxycarbonyl, lower-alkylthio-lower-alkoxycarbonyl, hydroxylower-alkyl, hydroxy, and oxo; and $R_5$ is from one to two, the same or different, substituents selected from the group consisting of hydrogen, lower-alkoxy, hydroxy, dilower-alkylamino-lower-alkoxy, carboxylower-alkoxy, nitro, polyhydroxylower-alkoxy, amino, epoxylower-alkoxy, carboxy, lower-alkanoylamino, lower-alkoxycarbonyl, pyridinyl, 4-morpholinyl-lower-alkoxy, lower-alkylsulfonyl, cyano, 1-imidazolyl, halogen, dilower-alkylaminosulfonyl, oxadiazolyl substituted onf any available carbon atom thereof by lower-alkyl, lower-alkylsulfinyl, 1-pyrazolyl, or 1-pyrazolyl substituted on any available carbon atom thereof by lower-alkyl, trifluoromethylsulfonyl, and lower-alkenyl.

13. The method of claim 12 wherein wherein $R_1$ is selected from the group consisting of ethyl, isopropyl, benzyl or cyclopentyl; $R_2$ is selected from the group consisting of hydrogen or methyl; and $R_3$ is selected from the group consisting of hydrogen, methyl, ethyl or hydroxymethyl.

14. The method of claim 13 wherein $R_4$ is cycloalkyl selected from the group consisting of cyclohexyl, cyclopropyl, and adamantyl or said cycloalkyl group substituted by one substituent selected from the group consisting of methoxycarbonyl, methylthiomethoxycarbonyl, hydroxymethyl, hydroxy, and oxo; and $R_5$ is from one to two, the same or different, substituents selected from the group consisting of hydrogen, methoxy, hydroxy, 2-(dimethylamino) ethoxy, carboxymethoxy, nitro, 2,3-dihydroxypropoxy, amino, 2,3-epoxypropoxy, 1-carboxyethoxy, carboxy, acetylamino, methoxycarbonyl, pyridinyl, 2-(4-morpholinyl) ethoxy, methylsulfonyl, cyano, 1-imidazolyl, bromo, diethylaminosulfonyl, 5-methyl-3-(1, 2,4-oxadiazolyl), methylsulfinyl, 4-methyl-1-pyrazolyl, 1-pyrazolyl, trifluoromethylsulfonyl, and ethenyl.

15. The method of claim 14 wherein the compound is 1-ethyl-6-nitro-N-[S(+)-1-(cyclohexyl)ethyl]-1H-pyrazolo [3,4-b]quinolin-4-amine.

* * * * *